(12) United States Patent
Harwanegg et al.

(10) Patent No.: US 11,740,232 B2
(45) Date of Patent: Aug. 29, 2023

(54) ANTIGEN ARRAY

(71) Applicant: Macroarray Diagnostics GmbH, Vienna (AT)

(72) Inventors: Christian Harwanegg, Vienna (AT); Georg Mitterer, Vienna (AT)

(73) Assignee: Macroarray Diagnostics GmbH, Vienna (AT)

( * ) Notice: Subject to any disclaimer, the term of this patent is extended or adjusted under 35 U.S.C. 154(b) by 1285 days.

(21) Appl. No.: 16/084,222

(22) PCT Filed: Mar. 30, 2017

(86) PCT No.: PCT/EP2017/057481
§ 371 (c)(1),
(2) Date: Sep. 11, 2018

(87) PCT Pub. No.: WO2017/167843
PCT Pub. Date: Oct. 5, 2017

(65) Prior Publication Data
US 2019/0079083 A1    Mar. 14, 2019

(30) Foreign Application Priority Data

Mar. 30, 2016    (EP) ..................................... 16162859

(51) Int. Cl.
*G01N 33/543* (2006.01)
*G01N 33/68* (2006.01)

(52) U.S. Cl.
CPC .  *G01N 33/54306* (2013.01); *G01N 33/54346* (2013.01); *G01N 33/54366* (2013.01); *G01N 33/68* (2013.01); *G01N 33/6854* (2013.01)

(58) Field of Classification Search
None
See application file for complete search history.

(56) References Cited

U.S. PATENT DOCUMENTS

| | | | | |
|---|---|---|---|---|
| 5,945,293 A * | 8/1999 | Siiman | ................. | G01N 33/548 435/7.1 |
| 6,268,222 B1 | 7/2001 | Chandler et al. | | |
| 9,488,648 B2 * | 11/2016 | Neely | ................. | G01R 33/1269 |
| 2002/0015666 A1 | 2/2002 | Vann et al. | | |
| 2005/0079592 A1 * | 4/2005 | Takagi | ................. | B01J 19/0046 435/174 |
| 2008/0176253 A1 | 7/2008 | Christodoulides et al. | | |
| 2012/0164644 A1 * | 6/2012 | Neely | ................. | C12Q 1/6895 435/6.15 |
| 2012/0183977 A1 * | 7/2012 | Bunce | ................. | G01N 35/1081 435/7.92 |
| 2013/0079237 A1 * | 3/2013 | Crisanti | ............. | G01N 33/6854 506/18 |
| 2015/0177233 A1 | 6/2015 | Puntambekar et al. | | |
| 2015/0293120 A1 * | 10/2015 | Lu | ....................... | G01N 33/6893 435/197 |
| 2016/0060687 A1 * | 3/2016 | Zhu | .................. | G01N 33/54313 506/31 |

FOREIGN PATENT DOCUMENTS

| | | |
|---|---|---|
| CN | 1430052 A | 7/2003 |
| CN | 1527943 A1 | 9/2004 |
| JP | 2005-077284 A | 3/2005 |
| WO | 32/029415 A1 | 4/2002 |
| WO | 2004104586 A1 | 12/2004 |

OTHER PUBLICATIONS

Tai, LW et al., Analytical Biochemistry, vol. 391, No. 2, 2009, pp. 98-105.
European Search Report, EP16162859 (dated Sep. 9, 2016).
International Patent Application No. PCT/EP2017/057481, International Search Report and Written Opinion, 11 pages (dated May 10, 2017).
Office Action for EP17714715.4 dated Mar. 20, 2020; 6 pages.
Office Action for corresponding Japanese Patent Application No. 2018-551824 dated Feb. 18, 2021; 3 pages.
First Office Action for corresponding Chinese Patent Application No. 201780025559.1 dated May 28, 2021; 25 pages.
Decision to grant corresponding European Patent Application No. 17714715.4, dated Jan. 28, 2021.
Intention to grant a European application and text of claims intended for grant for corresponding European Patent Application No. 17714715. 4, dated Dec. 2, 2020.

* cited by examiner

*Primary Examiner* — Ann Montgomery
(74) *Attorney, Agent, or Firm* — Loza & Loza, LLP; Michael Fedrick

(57) ABSTRACT

The present invention relates to antigen arrays and methods for the detection of immunoglobulins specific for any one of the antigens of the array in a biological sample. Specifically, the present invention relates to antigen arrays comprising groups of antigen-coated beads fixed on a solid support. Further encompassed herein are cartridges, kits and an apparatus comprising the antigen array and methods of using same.

19 Claims, 8 Drawing Sheets

Figure 1C

Figure 1A:
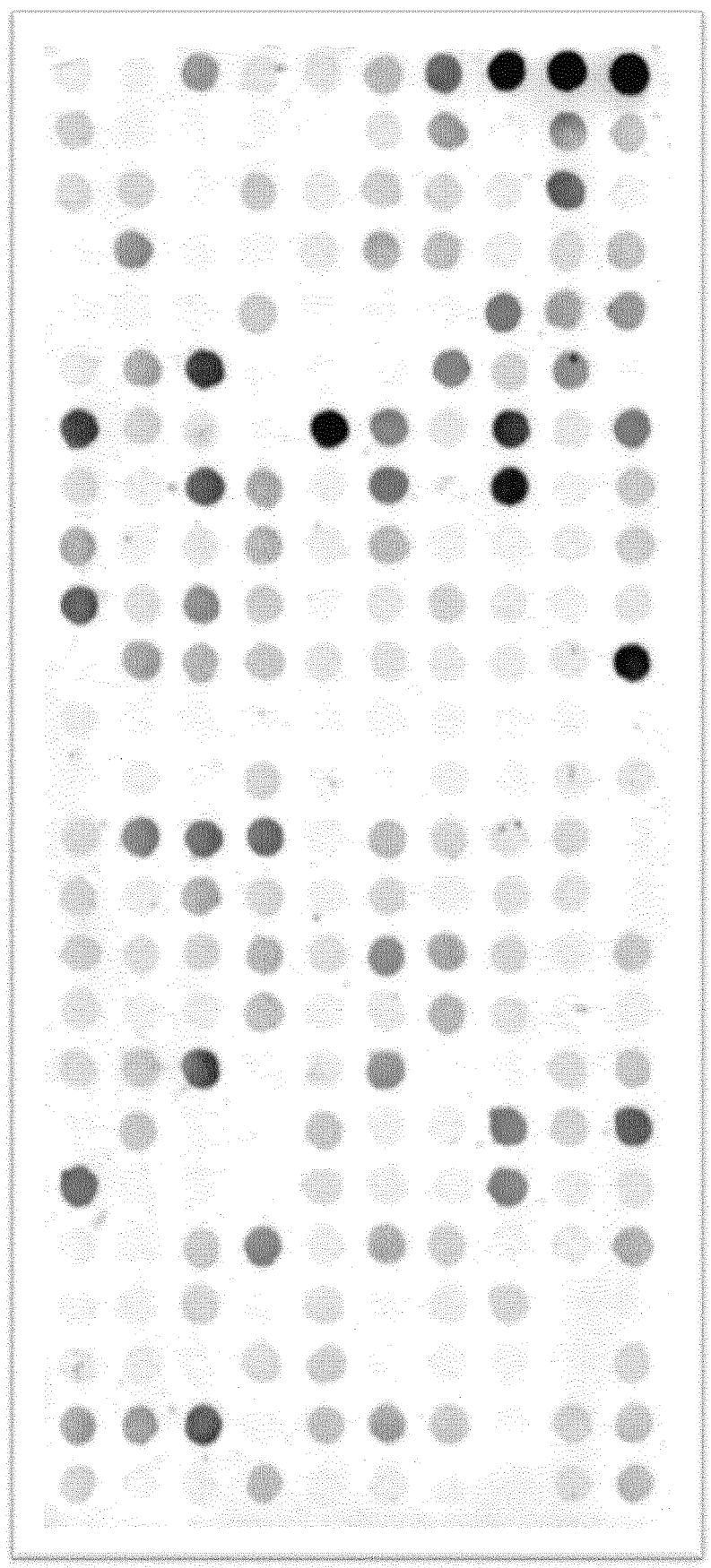

| Ven ga 1 | Ves spp | Vit v [Fruit] | Zea m [Seed] | Zea m 14 | IgE Std. 1 | IgE Std. 2 | IgE Std. 3 | IgE Std. 4 | IgE Std. 5 |
|---|---|---|---|---|---|---|---|---|---|
| Tri a [Seed] | Tri a 18 | Tri a 28 | Tri a 7k- | Buffer | Tri me | Tri tp | Uro du | Uro du 1 | Ven ga |
| Sola l [Fruit] | Sola l [Seed] | Sola l 6 | Sola m | Sola t | Sola t 1 | Spi o | Sus s [Meat] | Sus s 1 | Thu a [Meat |
| Rat n 1 | Rat n 4 | Sac c | Sal k 1 | Sal s [Meat | Sar m | Sec c [Seed] | Ses i [Seed] | Sin a [Seed] | Sol so |
| Pru p 3_A | Pru p 7 | Pun g | Pun g 1 | Pun g 14 | Pun g 5 | Pun g 7 | Que a [Polle | Que i [Polle | Rat n [Epith |
| Pin p [Seed] | Pis v [Seed] | Pla a [polle | Pla a 1 | Ple o [Spor | Pol spp | Pru ar [Fruit] | Pru du | Pru p [Pulp] | Pru p 3_B |
| Per a | Per a 7 | Pers a | Pha v [Seed] | Phl p | Phl p 1.010 | Phl p 2.010 | Phl p 5.010 | Phl p 6.010 | Phl p 7.010 |
| Ory s [Seed] | Ovi a [Meat] | Ovi a [Milk] | Ovi a 6 | Pan b | Par j | Par j 2 | Pas n | Pen ch | Pen m 1 |
| Mus m | Mus m 1 | Myt e | Nep n | Oct v | Ole e [Polle | Ole e 1 | Ole e 2 | Ory c [Meat] | Ory c 6 |
| Lol p 1 | Lup a [Seed] | Mal d [Fruit] | Mal d 1.010 | Mala p | Mel g [Egg | Mel g [Egg | Mel g [Meat | Mer a 1 | Mer mr 1 |
| Hom s HSA | Hom s LF | Hor v [Seed] | Jug r [Seed] | Jug r 3 | Lac s | Len c | Lep d | Lin us | Lol p [Polle |
| Hev b | Hev b 1 | Hev b 10 | Hev b 11 | Hev b 3.010 | Hev b 5.010 | Hev b 6.02 | Hev b 7.02 | Hev b 8 | Hev b 9 |
| Gal d 2 | Gal d 3 | Gal d 4 | Gal d 5 | Gly m | Gly m 1 | Gly m Agglut | Gly m TI | Hel as | Hel as 1 |
| Fel d | Fel d 1 | Fel d 2 | Foe v [Bulb] | Fra a | Fra a [ache | Gad m | Gal d [Egg | Gal d [Egg | Gal d 1 |
| Der p 10 | Der p 2 | Der p 23.01 | Der p 7 | Der p 9 | Equ as [Milk] | Equ c [Epith | Equ c [Milk] | Equ c 3 | Equ c Myogl |
| Cri c [Epith | Cry j | Cuc m [Pulp] | Cuc s | Cup a 1 | Cyn d [Polle | Dau c | Der f | Der p | Der p 1 |
| Cer si [Seed] | Che qu | Cic a | Cit r [Fruit] | Cla h | Coc n [Seed] | Cor a [Polle | Cor a [Seed] | Cor a 1.010 | Cor a 9 |
| Can f 1 | Can f 2 | Can f 3 | Cor a 8 | Cand a | Cap h [Milk] | Car p 1 | Car p Chym | Cas s [Seed] | Cav p [Epith |
| Bos d 6 | Bos d 8 | Bos d CA | Bos d Gelati | Bos d LF | Bos d TG | Bot fu | Bub b [Milk] | Cam d [Milk] | Can f [Epith |
| Bla g 1 | Bla g 2 | Bla g 4 | Bla g 5 | Blo t | Bos d [Epith | Bos d [Meat | Bos d [Milk] | Bos d 4 | Bos d 5 |
| Asp n | Asp r 1 | Aspa o | Ave s [Seed] | Ber e [Seed] | Bet v [Polle | Bet v 1.010 | Bet v 2.010 | Beta v [Leaf] | Bla g |
| Ara h 1-NT | Ara h 2 | Ara h 3 | Ara h 6 | Ara h 8.010 | Ara h Agglut | Arm r HRP | Art v | Art v 1 | Asp f |
| Ani pe | Ani s | Ani s 1 | Ani s 3 | Api g [Stalk] | Api g 1.010 | Api m [Veno | Api m 1 | Api m 4 | Ara h |
| All p | All s | Alt a 1 | Alt a 6.010 | Ama cr | Amb a | Amb a 1 | Ana c | Ana c 2 | Ana o [Seed] |
| Act c [Fruit] | Act c 11 | Act c Chitin | Act d [Fruit] | Act d 1 | Act d 10 | Act d 2 | Act d 5 | Aed c | All c |

Figure 2

Comparative test evaluation:
220 preselected multi-sensitized samples, ImmunoCAP ISAC test results available
30 allergenic components showed at least 5 positive values
779 positive results and 2772 negative results were analyzed for the below table

|  | Allergen | Sensitivity (*) | Specificity (*) | r2 correlation (**) |
|---|---|---|---|---|
| Mites | Der p 1 | 97 | 98 | 0,80 |
|  | Der p 2 | 78 | 90 | 0,65 |
|  | Der p 10 | 100 | 100 | 0,99 |
| Cat | Fel d 1 | 98 | 100 | 0,61 |
| Dog | Can f 1 | 100 | 99 | 0,75 |
|  | Can f 3 | 100 | 100 | 0,99 |
| Milk | Bos d 4 | 100 | 100 | 0,96 |
|  | Bos d 5 | 100 | 99 | 0,96 |
|  | Bos d 6 | 75 | 89 | 0,85 |
|  | Bos d 8 | 100 | 99 | 0,77 |
| Egg | Gal d 1 | 100 | 100 | 0,97 |
|  | Gal d 2 | 75 | 100 | 0,97 |
| Olive | Ole e 1 | 100 | 100 | 0,89 |
|  | Ole e 2 | 100 | 100 | 0,85 |
| Alternaria | Alt a 1 | 100 | 95 | 0,85 |
| Grass | Phl p 1 | 100 | 100 | 0,82 |
|  | Phl p 2 | 100 | 91 | 0,86 |
|  | Phl p 5 | 100 | 97 | 0,77 |
|  | Phl p 6 | 100 | 98 | 0,80 |
|  | Phl p 7 | 100 | 100 | 0,93 |
|  | Lol p 1 | 100 | 79 | 0,79 |
| Birch | Bet v 1 | 100 | 79 | 0,95 |
|  | Bet v 2 | 100 | 99 | 0,93 |
| Mugwort | Art v 1 | 100 | 99 | 0,56 |
| Cypress | Cup a 1 | 100 | 97 | 0,87 |
| Olive | Ole e 1 | 100 | 93 | 0,89 |
|  | Ole e 2 | 100 | 98 | 0,85 |
| Latex | Hev b 6.02 | 100 | 100 | 0,95 |
|  | Hev b 8 | 92 | 96 | 0,85 |
| Parietaria | Par j 2 | 95 | 97 | 0,84 |
|  | Averages | 97 | 96 | 0,85 |

(*) Sensitivity and specificity was evaluated using MedCalc, against reference data from ImmunoCAP ISAC using the manuacturers protocols for testing and cut-off 0.3 ISU
(**) Linear regression analysis of measurement results was performed with Microsoft Excel

Figure 5

Technical specifications and comparison of available multi-parameter assays for specific IgE measurements

| | FABER | ImmunoCAP ISAC |
|---|---|---|
| Manufacturer | Macro Array Diagnostics | Thermo Fisher Scientific |
| Allergen components (#) | 123 | 112 |
| Allergen extracts (complete allergens) (#) | 122 | 0 |
| Serum volume | 100 microliter | 35 microliter |
| Serum volume per reportable result | 0.4 microliter | 0.3 microliter |
| Test duration | 4 hours | 4 hours |
| Signal generation | Colorimetric, enzymatic amplification | Fluorescence, no amplification |
| Limit of detection | >= 0.1 kU/L for allergen components >= 0.3 kU/L for allergen extracts | >= 0.3 kU/L |
| Linear range | 0.1 50 Units (2.5 logs) end point measurement; 0.1 180 Units (3 logs) kinetic measurement | 0.3 100 Units (2.26 logs) not available |
| Readout | CCD/CMOS scanner or camera | Confocal Laser Scanner |
| Cost for scanner | ~ 20.000 Euro | ~ 19.000 Euro |
| Scanning duration/operation | ~ 30 seconds for 40 tests, manual | 2 minutes per 4 tests, manual procedure |
| Results analysis & duration | Fully automatic, < 5 sec per sample | Manual steps required, operator depending |
| Minimum samples per run | 1 | 4 |
| Maximum samples per run (1 operator, 1 day) | ~ 100 | < 100 |
| Calibration | Online (IgE standard curve) | Additional test & sample, heterologous |
| Allergen or batch specific correction | DataMatrix barcode based, batch and allergen | No |
| Automation | Manual or semi automatic | Manual |
| Storage of processed test before readout | Infinite | Days (if protected from light) |
| Test results | Arbitrary units. Semi quantitative(*) | Arbitrary units. Semi quantitative(*) |
| Precision (CV, tests) | < 15 % | 25 % > 1 ISU, > 35 % < 1 ISU |
| Stability / Storage | > 1 year, no real time data available | No data |
| Sample type | Serum, plasma | Serum, plasma |
| Hemolytic sample interferences | No | No data |
| Total IgE interferences | Not measurable > 5000 IU/mL IgE | Data not available |

ANTIGEN ARRAY

CROSS-REFERENCE TO RELATED APPLICATIONS

This application is the U.S. national stage of International Patent Application No. PCT/EP2017/057481, filed on Mar. 30, 2017 and entitled ANTIGEN ARRAY, which claims the benefit of priority under 35 U.S.C. § 119 from European Patent Application No. 16162859.9, filed Mar. 30, 2016. The disclosures of the foregoing applications are incorporated herein by reference in their entirety.

FIELD OF THE INVENTION

The present invention relates to antigen arrays and methods for the detection of immunoglobulins specific for any one of the antigens of the array in a biological sample. Specifically, the present invention relates to antigen arrays comprising groups of antigen-coated beads fixed on a solid support. Further encompassed herein are cartridges, kits and an apparatus comprising the antigen array and methods of using same.

BACKGROUND

Allergies and closely related diseases such as bronchial asthma affect one quarter of the population in the industrial nations. WHO names allergies a major health issue of the $21^{st}$ century. Currently, type 1 allergy affects almost one third of the population in the industrial nations. Though often harmless, the incidence and severity of allergies are increasing, as are the direct and indirect costs to society. In theory allergy diagnosis is a simple task, which still presents challenges to diagnostic industry and health care providers. A significant percentage of patients does not receive appropriate diagnosis and treatment. The consequences are reduced quality of life, avoidable deaths, and generally higher disease management costs. In order to optimize treatment for each individual patient, diagnosis cannot stop at the identification of an allergen source (e.g. a pollen, an animal, a food), but has to advance deeper into the molecular sensitization profile. The disease eliciting single allergen molecules must be identified correctly, since they are responsible for: cross-reactivity between allergen sources, risk classification (severe reactions or milder forms), type of symptoms (sneezing, asthma, etc.), choice of therapy; and prognosis for disease progression. This need for increased diagnostic resolution creates a multiplier for a number of parameters to be tested routinely, that is neither matched by the reimbursement systems, nor by the current technological capabilities of routine allergy diagnostic instrumentation.

Detection of specific immune responses in the form of specific antibody production against certain biological or non-biological antigen targets is thus key to the diagnosis of type I allergy but also for other immunological conditions such as autoimmune diseases and infectious diseases.

In all of these areas, the underlying condition can be caused by a variety of disease eliciting antigens which can act as markers for the disease, or antigens which serve as surrogate markers for a condition or prediction of outcomes as in the case of autoimmune diseases.

The term antigen in general refers to a substance that can cause the immune system to produce an antibody response against it, and possibly can trigger a biological reaction when an antibody binds to it under the appropriate in vivo conditions.

Theoretically, doing thorough anamnesis in the first step would allow to narrow the number of test parameters for the second step of in vitro testing to a reasonably low number. For a number of practical limitations however, this is not always easily achievable, which makes the application of multi-parameter diagnostic testing for several diseases attractive. This holds true in particular where an identical antibody class is responsible for the immune response against a multitude of antigens (e.g. IgE, IgG, IgA), so that multi-antigen based antibody response monitoring can facilitate a better health care for each individual patient. Using bioinformatics to identify antigen profiles or patterns or predictive algorithms can greatly facilitate diagnosis and treatment selection, and enable the physician to provide a more patient-tailored approach in treatment and monitoring of treatment.

In vitro tests for antigen specific immunoglobulin detection are mostly based on the ELISA principle, where an antigen is immobilized onto a solid phase, which is then incubated with a sample, and after washing off the non-bound sample and non-specific antibodies, the specifically bound antibodies are detected with a secondary antibody or an affinity binder of sorts generating a detectable signal known to those skilled in the art (color, photons, etc).

Immobilizing in this context refers to binding the antigen either by chemical coupling or other non-covalent ways of attachment to a solid phase, e.g. a plastic surface or any other solid carrier with suitable physical and chemical properties to retain the antigen.

A common complication when developing a multi-parameter immunological in-vitro test is the heterogeneous nature of the antigens, whereas the testing format can normally only apply identical or at least similar conditions for each antigen during both immobilization and the assay procedure. Consequently, this results in a tradeoff between the number of antigens to include in a test versus the technical performance of the test according to dimensions known to the skilled expert.

The vast majority of relevant antigens are proteins, either from biological sources such as foods, plants, bacteria or viruses, or as in case of autoimmunity, proteins produced by the human organism itself. Proteins—as compared for example to DNA in genetic testing—are extremely versatile but also extremely heterogeneous (charge, structure, stability, surface properties etc), and it is not only necessary to accommodate the physico-chemical properties of each protein during the handling and test manufacturing. Even more important, it is necessary to preserve the biological activity e.g. by keeping intact the secondary and tertiary structure of the biomolecules which create the actual epitopes and antibody binding sites. Otherwise a functional assay with clinically relevant sensitivity and specificity cannot be achieved.

Several relevant antigens in allergy, infectious or autoimmune diseases are not free or soluble proteins and need relatively harsh chemical solvents in order to stay in solution, which makes conventional protein coupling or handling in the manufacturing process of in vitro tests tedious. Examples for these are: storage proteins from nuts or seeds, or cellular antigens which are residing in cell membranes or within tissues where they are locally produced.

In the field of allergy in vitro diagnosis, a further complication is that the biological sources which contain the disease eliciting antigens are very heterogeneous between but also within the sources. Typically, so called allergen extracts are used for both in vivo and in vitro diagnosis. An allergen extract is an aqueous excerpt of the protein content from the respective source, like foods, animals, plants, plant pollen etc. In the allergen extracts, a complex and difficult to standardize mixture of allergenic and non-allergenic constituents is presented to the patient's skin or tested against the patients' blood sample, which can contain specific IgE antibodies.

Out of this complex mixture of proteins, lipids, carbohydrates and other chemical compounds, only a relatively small number of proteins or protein families in each allergen source are known to be actually allergenic in a way that they can cause the immune system to produce an antibody response.

This fraction of actually relevant antigen in a vast majority on irrelevant material places a high demand on the binding capability of the solid support material, and typically it is not possible to make a sensitive and specific IgE assay for allergy diagnosis on a simple plain surface such as an ELISA plate, without further enrichment of the allergenic fraction and removal of non-allergenic materials.

Over the last three decades, many of so called molecular antigens relevant in the diagnosis of allergies have been identified, and either purified from the natural source or produced by recombinant DNA technology. The use of molecular antigens has many advantages, from standardization to better understanding and prediction of molecular cross-reactivity, to risk classification of patients and adaptive treatment. However, a big disadvantage for any routine testing is that first, it requires much more expertise from the physician in the parameter selection for testing. Secondly, it creates significantly higher cost per patient if tested by conventional means of single parameter testing, which still accounts for more than 99% of the commercial market. Even more, the amount of blood that has to be drawn from the patient would rise in a linear way with each conventional single parameter test performed, typically in the range of 50 to 100 microliter per parameter.

Consequently, multi-parameter (also referred to as multiplexed) assay systems have been developed and made public by several groups, employing various basic technologies ranging from conventional miniaturized microtiter plate (MTP) based ELISA systems to suspension bead arrays or microarrays in various implementations.

For example, WO2004/104586A1 describes a method and device for detecting allergen-specific antibodies based on binding of such antibodies to a capture reagent (e.g. Protein A, Protein G or an antibody that specifically binds to immunoglobulins), which is attached to a biochip with a reactive surface. The bound allergen-specific antibody is then contacted with its respective allergen, which is detected by a labelled allergen-specific antibody.

US2005/079592A1 discloses a device for manufacturing a multiplexed bead assay where beads with a biological substance such as a protein fixed on their surface are ejected on a specific position on a solid phase base.

An assay for analysis of a plurality of analytes in a sample is further described in U.S. Pat. No. 6,268,222B1. The assay is based on core or carrier particles having a plurality of smaller fluorescently labelled polymeric particles or nanoparticles on their surface.

US2002/0015666A1 provides a system and process for storing and dispensing numerous selected reagents from a mass storage arrangement and Tai et al. ((Analytical Biochemistry, vol. 391, no. 2, August 2009, p. 98-105) describes a microfluidic cartridge and system for multiplexed immunoassays.

While suspension bead arrays theoretically can have a high degree of multiplexing in small volumes, the practical applications are limited to typically less than 20 parameters.

The intrinsic variability of the biological matrix such as serum or plasma makes it difficult for use in all routine labs where often hemolytic, lipemic or icteric sampes arrive for testing. Even more, the binding capacity allows only working with pure antigens, not, for example, with crude allergen extracts in sensitivity demanding applications like IgE detection. Moreover, the instrumentation is based on FACS (fluorescent activated cell sorting) or other expensive techniques, requiring several laser channels and confocal laser scanning precision.

Conventional microarrays on glass slides or inside microtiter plates can overcome some of the limitations of suspension beads by sacrificing the flexibility of mixing reagents on-demand as needed for each patient sample and the possibility to optimize each parameter fundamentally. In fact, having to use a flat and homogeneously active surface for binding of protein antigens is a significant inhibitor to achieve high-end performance. Moreover, the manufacturing is not only expensive but also highly complex due to the pico-liter quantities which need to be dispensed or deposited in a reproducible way. With currently on-the-market technology providers, there is no real high throughput capable instrumentation for producing millions of high quality diagnostic microarrays per year. Batch sizes are typically small (few hundreds or less) and Coefficients of Variability (CVs) are high compared to state of the art automated immunology analyzers. Similar to suspension bead technology, microarrays mostly work with fluorescence or luminescence readout and require expensive instrumentation also in this respect. Due to the miniaturized assay format, automation is not straight forward and requires sophisticated equipment and/or microfluidic designs, which again can be problematic with routine lab samples.

Other multi-parameter tests such as lateral flow type testing have the advantage of relatively low cost per parameter, but suffer from a lack of sensitivity, reproducibility, are seldom automated and cannot have more than 5-20 parameters per test strip.

Thus, in this segment of the clinical chemistry market there is currently no technology available that can serve all needs, in particular: low cost per test, high degree of multiplexing (>200), reproducibility, and excellent technical performance characteristics (CV, sensitivity, specificity, measurement range, quantification etc).

Therefore, it is the object of the invention to provide antigen arrays with significant improvement in reproducibility and excellent technical performance characteristics yet preserving a possibility to include many parameters and produce the test very cost efficiently.

SUMMARY OF THE INVENTION

The objective is specifically solved by the claimed subject matter.

Advances in molecular research and multiplex immuneassay technology are combined herein to form a one-stop-shop product for in vitro testing, namely an antigen array comprising groups of antigen-coated beads immobilized on a solid support. This novel array format and methods for producing and using same were developed based on the advantages of the state of the art methods from single parameter assays, mainly technical assay performance with the possibility of significant multiplexing while optimizing the coupling for each individual antigen, but without introducing significant trade-offs as compared to alternative methods, in particular regarding cost per test, scalability of manufacturing, or serum requirements per parameter. The miniaturized format such as in microarray testing is unsuitable for a cost effective yet high performance testing format, thus the antigen-array described in detail below can be considered an in vitro macro array test consisting of immobilized nano- or micro-particles which form discrete entities for each antigen-coupled bead population, but of significantly larger dimensions than conventional microarrays.

This novel technology allows individually optimized coupling of any antigen (e.g. detection antigen) such as an allergen to the solid phase, thereby enabling sensitive yet robust assay design, and eliminates the trade-off between cost effectiveness and individual test parameter performance. The antigen-array and methods provided herein improve the general sensitivity but in particular the sensitivity when working with heterogeneous source material in so far as the two phased coupling approach—first to particles and second to a solid phase or porous and 3D structured solid phase—creates a multiple amplification of the antigen presenting surface to which the antibodies can bind, during the assay incubation steps. State-of-the-art automation and software solutions complement the reagents.

Using intelligently designed panels of antigens combined with the robustness, sensitivity and specificity of the assay as well as its easy use, provides better clinical interpretation of the results and prediction of cross-reactivities, and thus selection of effective treatment methods.

Thus, the array and methods disclosed herein provide a first-time test that has the potential to change the routine of allergy diagnosis as well as other immunological conditions based on specific and reliable antibody detection such as infectious or autoimmune diesease. Specifically regarding allergy diagnosis, currently in-vitro tests are conducted as second or third step in the diagnostic process, but comprehensive, high-resolution yet sensitive screening tests as described herein can become a first level tool, only to be followed up by confirmatory anamnesis, skin tests or provocation. The benefits will apply to the whole value chain, but most importantly to patients suffering from immunological conditions.

Provided herein is in one aspect an antigen array comprising groups of antigen-coated beads fixed on a solid carrier, wherein each group comprises
(i) beads coated with one detection antigen, or
(ii) beads coated with a set of detection antigens, preferably wherein the solid carrier is a sheet or plate and the detection antigen is an allergen, an infection marker or an autoantigen.

In some embodiments, the detection antigen is a biomolecule made of nucleic acids and/or amino acids, preferably a protein, peptide, antibody or DNA molecule, or an organic or non-organic chemical compound.

In some embodiments, the detection antigen is an allergen.

In some embodiments, the detection antigen is an infection marker.

In some embodiments, the detection antigen is an autoantigen.

In some embodiments, the detection antigen is an antigen produced by recombinant DNA technology or an antigen isolated and purified from a biological material.

In some embodiments, where the beads are coated with a set of detection antigens, said set of detection antigens are obtained from an extract or lysate from a biological source material containing more than one antigen, or obtained from a purified fraction of such extracts or lysates or a purified fraction of cell culture derived materials.

In some embodiments, the detection antigen comprises a single epitope, a single macromolecule with several antibody binding epitopes or a mixture of various proteins with different antigens containing a variety of epitopes.

In some embodiments, the beads are micro- or nanobeads. Specifically, the beads have a size between 5 and 500 nm in diameter, preferably between 200 and 500 nm in diameter.

In some embodiments, the beads are latex beads, polymeric plastic beads, preferably polystyrene beads, beads made of biocompatible polymers, or glass beads, preferably silica beads. Specifically, the surface of the beads is porous or non-porous.

In some embodiments, the detection antigen is coupled covalently or non-covalently to the beads. Specifically, the detection antigen is coupled to the beads non-covalently by passive adsorption, preferably by hydrophobic and/or electrostatic attachment.

In some embodiments, the detection antigen is coupled via antigen spacers. Specifically, the detection antigen is coupled in a way that creates a preferred orientation for the presentation of epitopes presented on the bound antigen.

In some embodiments, the solid carrier is a sheet or plate of a porous or non-porous material, preferably a nitrocellulose sheet, more preferably a laminated nitrocellulose sheet.

In some embodiments, the array comprises at least 25 different groups. Specifically, the beads within the array or within one group are of the same or of different type. In some embodiments, the groups of antigen-coated beads are fixed on the solid carrier using contact methods or non-contact methods, preferably using a solenoid dispensing system. Specifically, each group is fixed as addressable element in a rectangular array, preferably at densities of 1 addressable element per mm$^2$.

In some embodiments, the beads of the antigen array described herein are of the same or different type. Specifically, the beads of different group of beads may be of the same type (e.g. all group of beads of the antigen array comprise polystyrene beads with a diameter between 200-500 nm), or the beads of different broup of beads may be of different types (e.g. group 1 comprises polystyrene beads, and group 2 comprises glass beads). Also the beads within one group may be of the same or different type.

In one aspect, provided herein is an allergen array comprising groups of allergen-coated beads fixed on a solid carrier, wherein each group comprises
(i) beads coated with one allergen, or
(ii) beads coated with a set of allergens, preferably an allergen extract, preferably wherein the solid carrier is a sheet or plate.

In a further aspect provided herein are methods of detecting an immunoglobulin specific for a detection antigen or for a set of detection antigens, preferably wherein the detection antigen or set of detection antigens is an allergen, an infection marker or an autoantigen, the methods comprising
(i) providing the antigen array according to any one of the antigen arrays described herein,
(ii) incubating the array with a sample,
(iii) incubating the array with a detection reagent,
(iv) optionally incubating the array with a signal generation reagent, and
(v) measuring a detectable signal.

In some embodiments, the immunoglobulin is an IgE antibody associated with allergy.

In some embodiments, the immunoglobulin is an IgG antibody associated with an infection or an autoimmune disease.

Further provided herein are methods of detecting an IgE antibody associated with allergy comprising
(i) providing an allergen array as described herein,
(ii) incubating the array with a sample,
(iii) incubating the array with a detection reagent, preferably an IgE-specific antibody or IgE-specific aptamer,
(iv) optionally incubating the array with a signal generation reagent, and
(v) measuring a detectable signal.

In some embodiments, the sample is a biological fluid, preferably serum, whole or processed blood, nasal fluid or urine, a cell lysate or a tissue homogenate from a subject or a pool of subjects.

In some embodiments, the detection reagent is an affinity binder specific for the immunoglobulin, preferably an antibody (e.g. an anti-IgE or anti IgG antibody), an aptamer (e.g. an IgE-specific aptamer or an IgG-specific aptamer) or an affibody. Specifically, the detection reagent is (i) directly labeled, preferably with a colored or fluorescent compound or with gold nanoparticles or colored latex nanoparticles; or (ii) conjugated to an enzyme (e.g. an anti-IgE or anti-IgG antibody with a directly detectable label or conjugated to an enzyme).

In some embodiments, the methods further comprise incubating the array with a signal generation reagent according to step (iv) of the method described herein, wherein the detection reagent is conjugated to an enzyme and the signal generation reagent comprises a substrate for said enzyme.

In some embodiments, the method further comprises incubating the antigen array described herein with a stop solution following step (iv) of the methods described herein, i.e. adding a stop solution after incubating the antigen array with a signal generation reagent to terminate signal generation.

Another aspect provided herein is a cartridge comprising a test chamber for any of the antigen arrays described herein, a reservoir for liquid waste, and optionally a barcode. The cartridge may further comprise reservoirs or integrated vials for any one or more of a detection reagent, a signal generation reagent, a stop solution, one or more buffers and one or more control samples.

Further provided herein is a kit comprising any of the antigen arrays as described herein, a detection reagent, one or more buffers, one or more control samples, instructions for using the kit in any of methods described herein, and optionally a signal generation reagent. The kit may further comprise a stop solution.

In another aspect, provided herein is an apparatus comprising a chamber for one or more cartridges as described herein, a pipettor and a device for signal detection.

FIGURES

FIGS. 1A and B: B/W representation of 245 allergens, specific IgE measurements and 5 IgE standards (top right corner) in increasing concentrations, after performing a standard assay with a human serum pool from allergic individuals (1A) or a negative control (1B) and scanning the image with a flatbed scanner. The original images were in 16-bit grayscale TIFF format.

FIG. 1C: schematic layout of allergen positions corresponding to FIGS. 1A and B. Each allergen feature was approx. 600 microns in diameter, distance between the features was 1 mm in each direction.

FIG. 2: Test evaluation by comparison to reference method.

Figure 3:
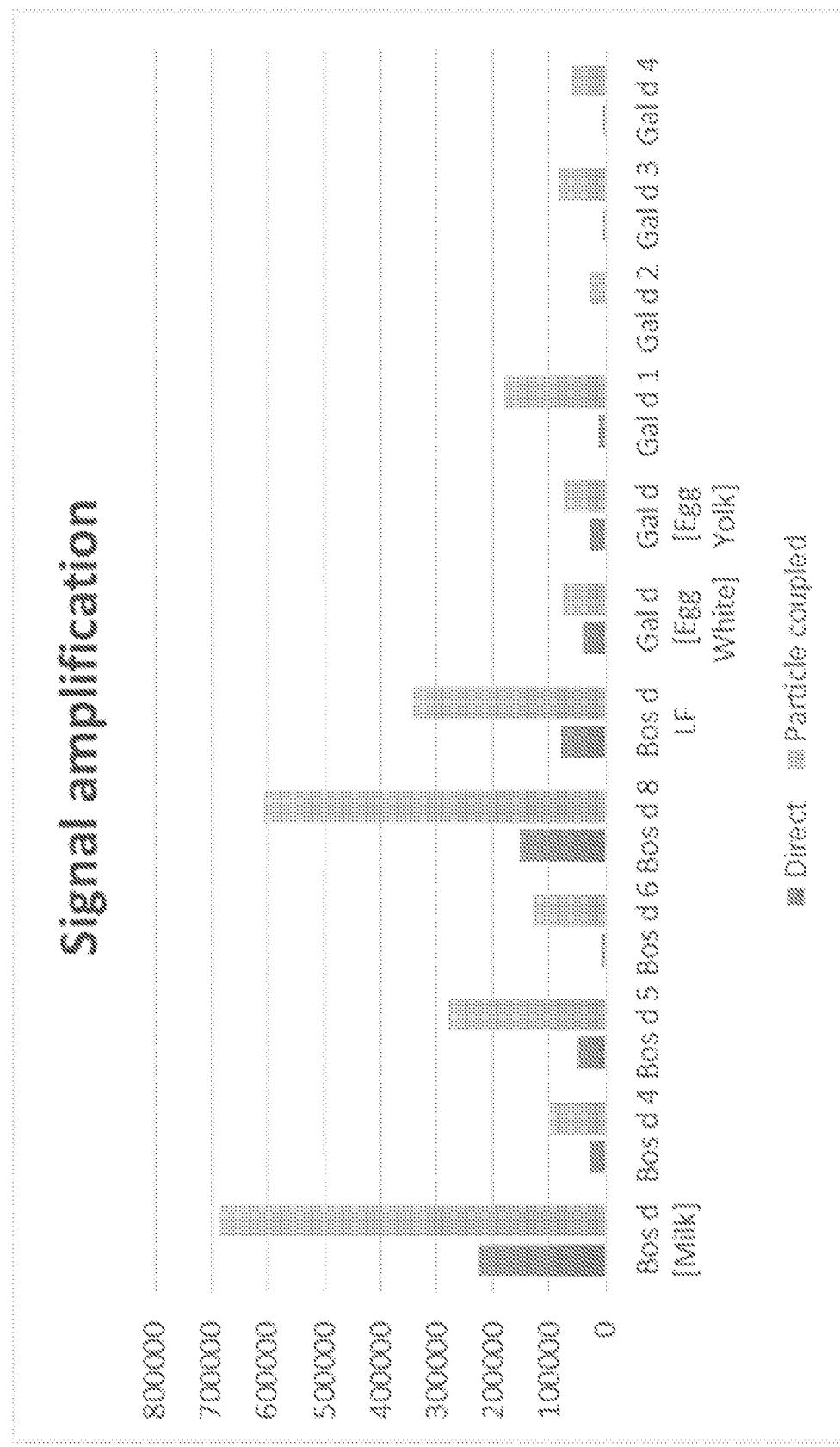

FIG. 3: Comparison of an array with molecular allergens directly immobilized on a solid support and an array with nanoparticles coupled with the same molecular allergens and immobilized on the same type of solid support. Graphic representation of results from Table 4.

Figure 4:
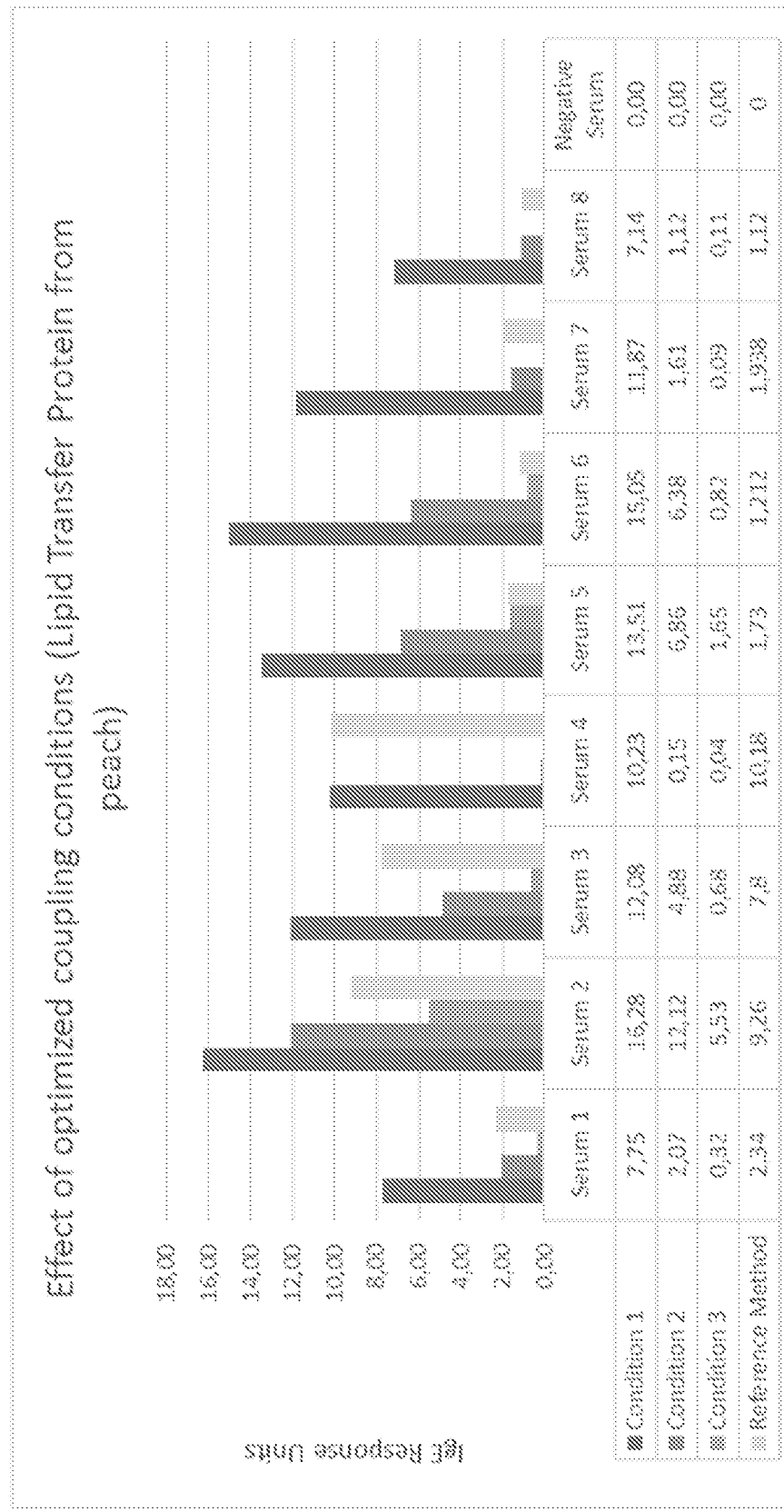

FIG. 4: Specific IgE measurements with 8 different samples positive and one negative against Pru p 3, a major allergen from peach.

FIG. 5: Technical specifications and comparison of available multi-parameter assays for specific IgE measurements. (*) specific IgE measurements by definition are semi-quantitative as no international reference standard preparation for individual allergens is available. (**) Average linear correlation from testing >100 samples and comparing allergen components and allergen extracts with ImmunoCAP and ImmunoCAP ISAC.

Figure 6:
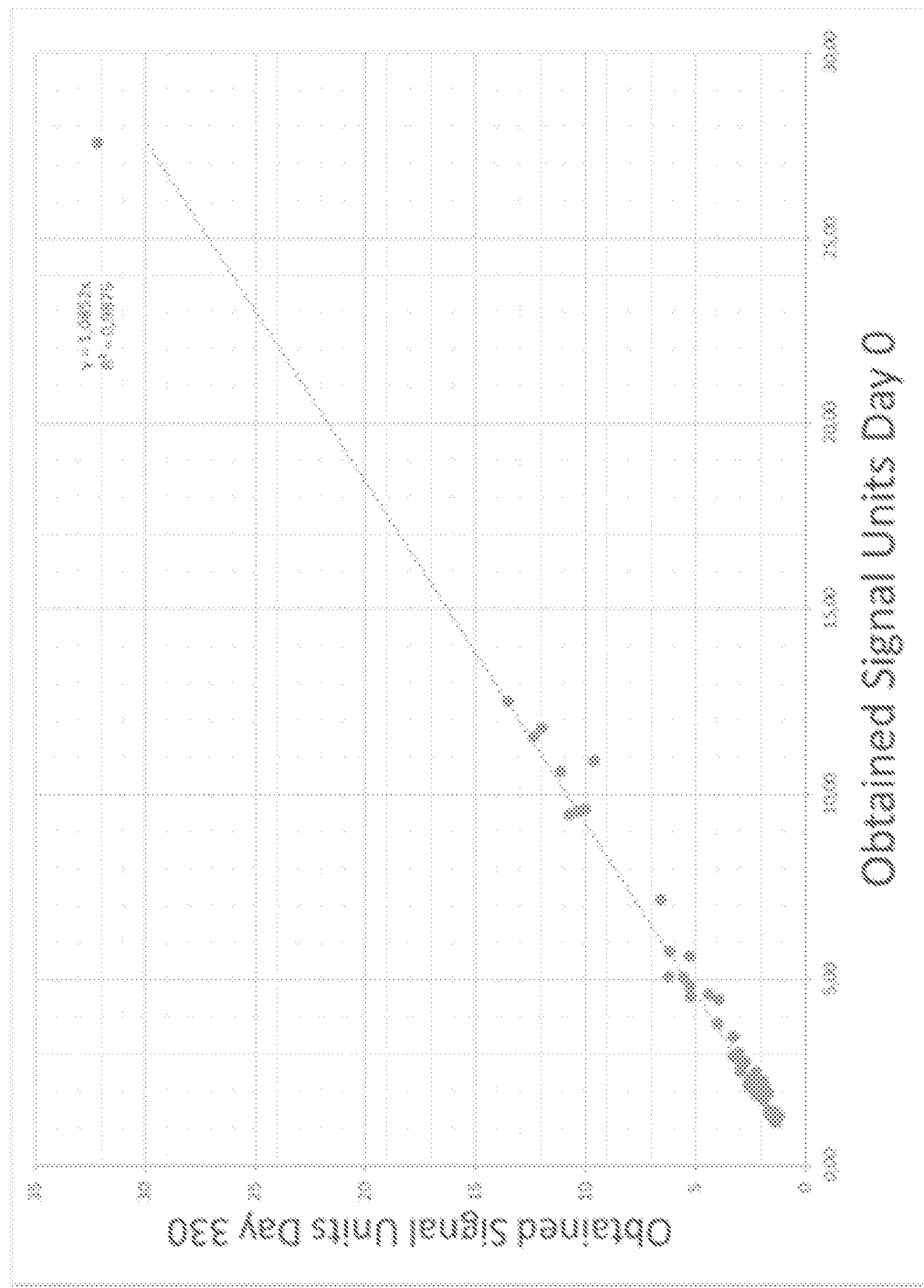

FIG. 6: Comparison of IgE measurements of a sample tested on day 0 and day 330 using the same preparation of allergen coated beads.

DETAILED DESCRIPTION OF THE INVENTION

Specific terms as used throughout the specification have the following meaning.

The term "antigen" as used herein refers to a substance that can cause the immune system to produce an antibody response against it, and possibly can trigger a biological reaction when an antibody binds to it under the appropriate in vivo conditions. The term antigen as used herein shall refer to a whole target molecule or a fragment of such molecule recognized by an antigen binding site. Specifically, substructures of an antigen, e.g. a polypeptide or carbohydrate structure, generally referred to as "epitopes", which are immunologically relevant, may be recognized by such antigen binding site.

The term "detection antigen", "antigen to be detected" or "detectable antigen" refers to an antigen determining an antigen-specific reaction, such as an antibody-antigen reaction. The term "antigen", "detection antigen", "antigen to be detected" and "detectable antigen" are used herein interchangeably.

The term "set of detection antigens" refers to one or more antigens determining a reaction specific for a condition. The condition may be a disease or disorder or a disposition therefor, such as allergy or an autoimmune disease; the term includes conditions that do not show any physical and/or clinical symptoms. The reaction specific for the condition may be an antibody-antigen reaction with at least one antibody that is characteristic for/associated with said condition and the condition can be determined by such reaction; for example, an IgE antibody specific for an allergen if the condition is an allergy. The term "set of antigens" as used herein refers to one or more antigens obtained from the same biological source material, e.g. obtained from a cell lysate, cell or tissue homogenate or a purified fraction thereof.

The term "epitope" refers to that portion of an antigen that determines its immunological specificity. The term epitope as used herein shall in particular refer to a molecular structure which may completely make up a specific binding partner or be part of a specific binding partner to a binding site of an antibody. An epitope may either be composed of a carbohydrate, a peptidic structure, a fatty acid, an organic, biochemical or inorganic substance or derivatives thereof and any combinations thereof.

Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding the polypeptide to form a tertiary structure and the amino acids are not necessarily adjacent to one another in the linear sequence. Specifically, and with regard to polypeptide antigens, a conformational or discontinuous epitope is characterized by the presence of two or more discrete amino acid residues, separated in the primary sequence, but assembling to a consistent structure on the surface of the molecule when the polypeptide folds into the native protein/antigen.

Commonly, an epitope is a polypeptide or polysaccharide in a naturally occurring antigen. Normally, a B-cell epitope will include at least about 5 amino acids but can be as small as 3-4 amino acids. Epitopes represent shapes recognized by immune B and T cells, and can also be represented by non-antigen derived peptides and other molecules that possess the same epitope shape that is present within the native antigen. An example of an element with an epitope shape is an aptamer. An aptamer is a molecule that provides a shape that can mimic an immunologic epitope. Portions of molecules such as peptides or molecules representing post-translational modifications, carbohydrates, lipids and other molecules can be used to represent individual epitopes.

The term "array" refers to a collection of groups of antigen-coated beads, where each group represents a spatially separated addressable element. Such elements or molecular entities can be spatially addressable, such as arrays contained within microtiter plates, or immobilized on planar surfaces where each element is present at distinct X and Y coordinates. For such spatial addressability, also known as coding, the position of the molecule is fixed, and that position is correlated with the identity, thereby allowing identification of the specificity of the antibodies contained within the sample to be tested in the array. This type of spatial array is generally synthesized or spotted onto a planar substrate, producing a large number of different elements densely laid out in a small area.

Unless specified otherwise, the terms "particles", "nanoparticles", "spheres", "microspheres", and "beads" as used herein are interchangeable and refer to small inert supports of round, oval or spherical shape which are susceptible to coating with an antigen (detection antigen) or a set of antigens (set of detection antigens).

The term "group of beads" as used herein refers to a population of beads coupled or coated (used herein interchangeably) with a specific detection antigen which can be identified with an antibody specific for said antigen in an antibody-antigen reaction or a population of beads coated with a set of detection antigens which can be identified with at least one antibody specific for one of the detection antigens of the set.

The term "type of bead" refers to the characteristic of the beads defined by their size, material, molecular properties of the surface coating, hydrophobicity, electric charge, surface properties (porous or non-porous surfaces), coupling chemistry or chemical linker/spacer chemistry. Beads of the same type have the same size, material, surface property and the same chemistry is used for coupling an antigen. Beads of a different type contemplate beads which differ in at least one of these characteristics.

As used herein, "support", "solid support", "carrier", "solid carrier" or "solid phase" refers to any solid surface onto which addressable elements/molecular entities (antigen coated beads) can be deposited and immobilized for conducting assays and reactions.

The term "immobilized" or "fixed" is used herein interchangeably and means that a material or particle, specifically an antigen-coated bead is bound either covalently or non-covalently to a solid support. The term refers to the material or particle being relatively stationary and not released during incubation and or washing steps performed with the solid support.

The term "immunoglobulin (Ig)" refers to the immunity-conferring portion of the globulin proteins of serum, and to other glycoproteins that have the same functional characteristics. They typically comprise four polypeptide chains—two identical light chains and two identical heavy chains that are linked together by disulfide bonds.

The term "IgG" refers to one of Ig isotypes found in serum, which is the main antibody raised in response to an antigen and has four major subtypes, IgG1, IgG2, IgG3 and IgG4.

The term "IgE" refers to one of Ig isotypes found in serum, which binds tightly to mast cell and basophils, and when additionally bound to antigen, causes release of histamine and other mediators of immediate hypersensitivity. This isotype of Ig plays a primary role in the predominant type I allergic reactions such as hay fever, asthma and anaphylaxis.

The term "antibody" as used herein refers to polypeptides or proteins that consist of or comprise antibody domains, which are understood as constant and/or variable domains of the heavy and/or light chains of immunoglobulins, with or without a linker sequence. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g. to modify the antigen binding properties or any other property, such as stability or functional properties, such as binding to the Fc receptors FcRn and/or Fcgamma receptor. The term "antibody" applies to antibodies of animal origin, including human species, such as mammalian, including human, murine, rabbit, rat, goat, lama, cow and horse, or avian, such as hen, which term shall particularly include recombinant antibodies which are based on a sequence of animal origin.

Antibodies may exist as intact immunoglobulins, or as modifications in a variety of forms including, for example, an Fv fragment containing only the light and heavy chain variable regions, a Fab or (Fab)'2 fragment containing the variable regions and parts of the constant regions, a single-chain antibody, and the like. The antibody may be of animal (especially mouse, goat, rabbit or rat) or human origin or may be chimeric. As used herein the term "antibody" includes these various forms, which may be produced by the modification of whole antibodies and/or synthesized de novo using recombinant DNA methodologies. "Monoclonal" antibodies refer to individual antibodies or populations of individual antibodies in which the antibodies are identical in specificity and affinity except for possible naturally occurring mutations that can be present in minor amounts.

The term "label" as used herein refers to a detectable compound or composition which is conjugated directly or indirectly to an antibody or antibody fragment so as to generate a "labeled" antibody/antibody fragment or a "detection antibody". The label may be detectable by itself, e.g. radioisotope labels, color or fluorescent labels, gold nanoparticles or colored latex nanoparticles or, in the case of an enzymatic label, may catalyze chemical alteration of a substrate compound or composition which is detectable.

The term "extract" as used herein refers to one or more substances, typically in concentrated form, obtained by treating a material such as a biological material, from which the extract is isolated, with a solvent, after which the solvent is removed. The term "extract" will also be understood to encompass the one or more substances obtained by subjecting a primary extract to subsequent purification processes known to those skilled in the art. Generally, an extract comprises a mixture of proteins and other molecules.

An allergen extract is typically prepared by extraction of allergen(s) from a biological source material. The biological source material is typically a multicellular or non-cellular material from a multicellular organism of the fungi, plantae or animal kingdom, or in some instances of bacterial origin. Such allergen extract may be obtained by aqueous extraction of water soluble material using mechanical homogenization procedures (e.g., vigorous mixing and stirring) followed by purification steps like filtration or fractioning to obtain the solution i.e. the extract. The extract may then be subjected to further purification and/or processing like freeze-drying removing substantially all the water. Generally, an allergen extract comprises a mixture of proteins and other molecules.

In the present context the term, "allergen" refers to any naturally occurring protein, its isoforms, a modified protein, a recombinant protein, a recombinant mutant protein, or any protein fragment thereof or mixtures of proteins that are capable of inducing allergic, i.e. IgE mediated reactions upon their repeated exposure to an individual. The term "set of allergens" as used herein refers to one or more allergens obtained from the same biological allergen source material, e.g. obtained from an allergen extract of a biological allergen source material.

The term "biological source material" or "biological material" refers to any material originating from any living organism. It particularly contemplates separated cells, pieces of tissue, bacteria, viruses, yeast, and sub-fractions (such as separated nuclei or cytoplasm) of many of the previous sources (comprising one or more antigens).

The expression "biological allergen source material" as used herein refers to any biological material comprising one or more allergens. Examples of such materials are acarids PMB (Pure Mite Body) or WMC (Whole Mite Culture), defatted or non-defatted pollens from e.g. grasses, herbs, weeds and trees, animal hair and dander, pelt, fungi mycelia and spores, insect bodies, venom or saliva and foods.

The term "autoimmune disease" includes any diseases associated with pathogenic autoantibodies, diseases which are most probably T cell mediated and diseases for which evidence for a pathogenic process is only direct. Said disorders may be, but are not limited to acute idiopathic thrombocytopenia, autoimmune haemolytic anaemias, autoimmune neutropenia, autoimmune erythroblastopenia, myasthenia gravis, Guillain-Barré syndrome, chronic inflammatory demyelinating polyneuropathy, multiple sclerosis, monoclonal gammopathies with anti-mag activity, adrenoleucodystrophy, Grave's disease, systemic lupus erythematosus, anti-cardiolipin antibodies and recurrent abortions, refractory polymyositis, juvenile rheumatoid arthritis, rheumatoid arthritis, Felty's syndrome, ulcerative colitis, Crohn's disease, certain glomerulonephritides, ANCA positive systemic vasculitis, Kawasaki's disease, anti-factor VIII autoimmune disease and birdshot retinopathy.

The term "covalent bond" or "covalent interaction" refers to bonds or interactions created by the sharing of a pair of electrons between atoms. Covalent bonds/interactions include, but are not limited to atom bonds, homopolar bonds, σ-σ-interactions, σ-π-interactions, two-electron-to-center bonds, single bonds, double bonds, triple bonds, as well as combinations of these interactions/bonds. The mentioned interactions/bonds, can be polar or polarized, or can be non-polar or non-polarized.

"Non-covalent" refers to associations between atoms and molecules such as ionic interactions (e.g., dipole-dipole interactions, ion pairing, and salt formation), hydrogen bonding, non-polar interactions, inclusion complexes, clathration, van der Waals interactions (e.g., pi-pi stacking), and combinations thereof.

The term "passive adsorption", "adsorption" or "absorption" refers to adhesion of atoms, ions or molecules from a gas, liquid or dissolved solid to a surface. The mechanism for adsorption is based primarily on hydrophobic (Van der Waals, London Type) attractions between the hydrophobic portions of the adsorbed molecule and the surface. Most hydrophobic molecules adhere to a surface by passive adsorption. In the case of less hydrophobic molecules (or more hydrophilic surfaces, such as —COOH or NH2 modified surfaces), attachment via both ionic interactions and hydrophobic interactions can take place.

The term "electrostatic interaction" or "electrostatic attachment", as used herein, refers to any interaction occurring between charged components, molecules or ions, due to attractive forces when components of opposite electric charge are attracted to each other. Examples include, but are not limited to: ionic interactions, covalent interactions, interactions between an ion and a dipole (ion and polar molecule), interactions between two dipoles (partial charges of polar molecules), hydrogen bonds and London dispersion bonds (induced dipoles of polarizable molecules).

A "detectable signal" refers to a physical or chemical signal, which can be measured by visual or instrumental methods, and includes colorimetric, fluorescent, electrical and chemiluminescent signals.

A "control value" or "control signal" refers to a reference value to which a signal obtained with a sample of a subject or pool of subjects can be compared. A negative control signal can be obtained, for example, (i) with a sample that does not contain any immunoglobulin(s), (ii) with beads that are not coated with any antigen, i.e. uncoated beads immobilized on a solid support, (iii) a solid support material by itself without any beads fixed onto it, or (iv) with a sample from a healthy individual or a pool or group of healthy individuals. A "positive control signal" can be obtained, for example, with a commercial reference sample with a specified amount of analyte (i.e. total immunoglobulin or defined immunoglobulin with specificity for a particular antigen/allergen), a sample that has been validated or tested positive in a standard assay, or with beads coupled with a specified amount of Immungolublin to be detected and fixed on the solid support.

The term "sample" refers to virtually any liquid sample. The sample can be derived from any desired source, such as a physiological fluid, for example, blood, saliva, ocular lens fluid, cerebral spinal fluid, sweat, urine, milk, ascites fluid, mucous, synovial fluid, peritoneal fluid, amniotic fluid or the like. The liquid test sample can be pretreated prior to use, such as preparing serum or plasma from blood, diluting viscous liquids, or the like; methods of treatment can also involve separation, filtration, distillation, concentration, inactivation of interfering components, and the addition of reagents. In addition, a solid can be used once it is modified to form a liquid medium. The term applies to any bodily fluid that can be used in an in vitro assay.

The term "subject" or "patient" as used herein shall refer to a warm-blooded mammalian, particularly a human being or a non-human animal.

The term "biomolecule" refers to any organic molecule that is part of a living organism. Biomolecule includes a nucleotide, a polynucleotide, an oligonucleotide, a peptide, a protein, a carbohydrate, a glycosylated molecule, a lipid, among others. The term as used herein also applies to organic molecules mimicking the structure and binding specificities of a biomolecule, e.g. an aptamer, thus being recognized by the same antibody as the biomolecule.

"Recombinant DNA technology" refers to molecular biology procedures to prepare a recombinant nucleic acid sequence as described, for instance, in Laboratory Manuals edited by Weigel and Glazebrook, 2002 Cold Spring Harbor Lab Press; and Sambrook et al., 1989 Cold Spring Harbor, N.Y.: Cold Spring Harbor Laboratory Press.

The term "antigen spacers" refers to chemical linkers which can be used to introduce an intermediate layer creating a defined distance between a solid surface and a coupled antigen, as well as defining the chemical properties said intermediate layer, for instance in: Bioconjugate Techniques, Greg T. Hermanson, Academic Press, 25 Jul. 2013

It is an object of the invention to provide an antigen array comprising groups of antigen-coated beads fixed on a solid carrier. In some embodiments, the antigen-coated beads are beads coated with one detection antigen (e.g. an antigen produced by recombinant DNA technology or an isolated and purified antigen from a biological source). In some embodiments, the antigen-coated beads are beads coated with a set of detection antigens (e.g. antigens obtained from an extract such as an allergen extract, antigens obtained from a lysate such as a bacterial cell lysate, antigens obtained from a cell or tissue homogenate or a purified fraction thereof).

For example, a first group of beads is coupled with a certain (first) detection antigen produced by recombinant DNA technology, a second group of beads is coupled with a different (second) detection antigen purified from a biological material, a third group is coupled with a set of detection antigens, which are again different from the first and second detection antigen, which set of detection antigens is obtained from a cell lysate, a fourth group of beads with yet another set of detection antigens, which is obtained from an extract, and so on. Thus, the different groups of antigen-coated beads (population of beads) of the antigen array differ in the antigen (e.g. detection antigen or set of detection antigens) coupled to it.

Such groups of beads bearing different detection antigens or set of detection antigens can be produced using different sources (e.g. lysate, extract, recombinant production) of detection antigen, different type of beads (beads of different size and/or material) and/or different coupling chemistries (non-covalent or covalently coupled antigens).

The antigen array described herein comprises at least 25 different groups of beads. In some embodiments, the antigen array described herein comprises at least any of 25, 50, 75, 100, 125, 150, 175, 200 or 250 groups of beads. In some embodiments, the antigen array comprises up to any one of 300, 400, 500 or 1000 groups of beads. In some embodiments, the antigen array comprises between 200 to 500 groups of beads, preferably between 250 and 350 groups of beads.

In some embodiments, the groups of beads within the antigen array comprise beads of only one type (e.g. only polystyrene beads, only beads of 200-500 nm diameter, etc.). In some embodiments, the groups of beads within the antigen array comprise groups with different types of beads (e.g. polystyrene beads of 350 nm diameter, latex beads of 300-500 nm diameter and glass beads of 5-500 nm diameter). In some embodiments, the groups of beads within the antigen array are produced using the same coupling chemistry (e.g. different detection antigens/set of detection antigens are coupled to different groups of beads via passive adsorption). In some embodiments, the couping chemistry differs between different groups of beads (e.g. a first detection antigen/set of detection antigens is coupled to a first group of beads using passive adsorption and a second detection antigen/set of detection antigens is coupled to a second group of beads using a covalent linker). Specifically, the antigen array may comprise a first group of beads comprising polystyrene microbeads with a diameter of about 200 nm where a first detection antigen is coupled to the surface via passive adsorption, a second group of beads comprising polystyrene microbeads with a diameter of about 500 nm and NH2 surface coating where a second detection antigen is coupled to the surface via the EGS (ethylene glycol bis(succinimidyl succinate)) crosslinker which introduces a 12 atom spacer, a third group of beads comprising polystyrene microbeads with a diameter of about 200 nm and COOH surface coating where a third detection antigen is coupled to the surface via the zero length EDC carbodiimide coupling chemistry.

In some embodiments, the beads within one group of beads (i.e. a population of beads coated with the same detection antigen or a population of beads coated with the same set of detection antigens) comprise beads of the same type. In some embodiments, the beads within one group of beads (i.e. a population of beads coated with the same detection antigen or a population of beads coated with the same set of detection antigens) comprise different types of beads. For example, within one group of beads, some beads (a first sub-population/type of beads) are beads with a diameter of about 200 nm, while some other beads (a second sub-population/type of beads) have a diameter of about 350 nm. In some embodiments, beads of a diameter of about 200 nm are preferentially coupled with a first detection antigen by mixing an extract or lysate (i.e. a mixture of proteins and other molecules) with said beads of 200 nm, and beads of a diameter of 350 nm are preferentially coupled to a second detection antigen by mixing them with the same extract, and then pooling the two types of beads coupled with the two different detection antigens obtained from the same extract or lysate, thereby creating a group of beads of different types coated with a set of detection antigens.

In some embodiments, the antigen array described herein is an allergen array comprising at least any one of 25, 50, 75, 100, 125, 150, 175, 200, or 250 groups of beads coupled with a detection allergen (e.g. an allergen produced by recombinant DNA technology or a purified natural allergen) or a set of detection allergens (e.g. beads coupled with an allergen extract). In some embodiments, the allergen array comprises up to any one of 300, 400, 500 or 1000 groups of beads. In some embodiments, the allergen array comprises between 200 to 500 groups of beads, preferable beween 250 and 350 groups of beads.

In some embodiments, the allergen array comprises one or more groups of beads coated with a molecular/recombinantly produced allergen, one or more groups of beads coated with an allergen extract, and/or one or more groups of beads coated with one or more allergens isolated and purified from a biological source.

In some embodiments, the antigen or allergen array described herein comprises at least 200 groups of beads (e.g.

between 200 and 300 groups of beads) fixed on a solid plate or sheet (e.g. a nitrocellulose membrane), wherein the array comprises (i) groups of beads (group A beads), each group (of group A beads) coated with a different detection antigen/allergen (e.g., group 1 coated with recombinantly produced first antigen/allergen, group 2 coated with a second antigen/allergen purified from an extract or lysate, group 3 coated with a recombinantly produced third antigen/allergen, etc.) and (ii) groups of beads (group B beads), each group (of group B beads) coated with a different set of detection antigens/set of allergens (e.g. group I coated with a first antigen/allergen extract obtained from a first biological material, group II coated with a second antigen/allergen extract obtained from a second biological material), and wherein the groups of beads (both beads of group A and group B) are beads made (e.g. polystyrene beads) with a diameter of about 200 to 500 nm (e.g. a diameter of about 350 nm) and the detection antigens/allergens or set of detection antigens/set of allergens are coupled to the beads covalently or non-covalently via the same or different coupling chemistries. In some embodiments, the different detection antigens/allergens or sets thereof are coupled to the beads via passive adsorption. In some embodiments, part of the detection antigens/allergens or sets thereof are coupled via passive adsorption while other detection antigens/allergens are coupled covalently, e.g. via EGS linkers or EDC chemistries.

In some embodiments, the groups of beads are arranged on the antigen or allergen array described herein in a rectangular pattern of rows and columns. In some embodiments, the antigen or allergen array described herein further comprises positive and/or negative control spots at defined positions in the array (e.g. marker spots) which can be used to locate and identify the antigen-coated beads of the array.

Antigens

Antigens are substances that can cause the immune system to produce an antibody response against it. Antigens are typically macromolecules or molecules such as proteins, peptides, antibodies polysaccharides, polynucleotides, RNA, DNA, lipids, glycosylated molecules, carbohydrates, organic or non-organic chemical compounds, naturally occurring modifications of such molecules, aptamers) that are foreign to the host. Antigens comprise one or more immunologic epitopes.

The antigens described herein are detection antigens, i.e. antigens determining an antigen-specific reaction. In some embodiments the detection antigens are allergens, infection markers and/or autoantigens.

Allergens are antigens capable of stimulating a type-I hypersensitivity reaction in atopic individuals through Immunoglobulin E (IgE) responses. Allergens may be contained within or derived from a food item such as, e.g., dairy products (e.g., cow's milk), egg, celery, sesame, wheat, soy, fish, shellfish, sugars (e.g., sugars present on meat such as alpha-galactose), peanuts, other legumes (e.g., beans, peas, soybeans, etc.), and tree nuts. Alternatively, an allergen may be contained within or derived from a non-food item such as animal products, e.g., dust mite excretion, fur and dander, wool; pollen, e.g., tree pollens (such as birch pollen, cedar pollen, oak pollen, alder pollen, hornbeam pollen, *aesculus* pollen, willow pollen, poplar pollen, *plantanus* pollen, *tilia* pollen, *olea* pollen, Ashe juniper pollen, and *Alstonia scholaris* pollen) weeds (ragweed, *plantago*, nettle, *Artemisia vulgaris, Chenopodium album*, sorrel) grass (rye grass, timothy grass); insect venom (e.g., venom of bees, wasps, mosquitos, fire ants, etc.), mold, latex, metals (e.g., nickel), household cleaners, detergents, medication, cosmetics (e.g., perfumes, etc.), drugs (e.g., penicillin, sulfonamides, salicylate, etc.), therapeutic monoclonal antibodies (e.g., cetuximab).

In some embodiments, the allergen is a cross-reactive allergen. Cross-reactive allergens are allergens of one source (e.g. birch) which share structural similarities to allergens of a different source (e.g. apple). Once a patient is allergic to the first source, he/she is likely to develop also an allergy to the second source. In some embodiments, the allergen is a marker allergen. Marker allergens are predominantly found in one specific source. In some embodiments, the allergen is a pan-allergen. Pan-allergens (e.g. profilins) are present in various different sources. In some embodiments, the allergen is a major allergen, which induces the predominant Ig response in the allergic population, whereas in another embodiment the allergen can be a minor allergen, which only a minority of allergic patients reacts to. In some embodiments, the allergen is an allergen which does not cross-react with any other allergen.

TABLE 1

List of allergens

| Code | Name | Species | Common name | Source | Kingdom |
|---|---|---|---|---|---|
| 2405 | Act c [Fruit] | *Actinidia chinensis* | Gold Kiwi | Fruit | Plants |
| 8234 | Act c 11 | *Actinidia chinensis* | Gold Kiwi | Fruit | Plants |
| 10879 | Act c Chitinase_IV | *Actinidia chinensis* | Gold Kiwi | Fruit | Plants |
| 1697 | Act d [Fruit] | *Actinidia deliciosa* | Green Kiwi | Fruit | Plants |
| 1 | Act d 1 | *Actinidia deliciosa* | Green Kiwi | Fruit | Plants |
| 5737 | Act d 10 | *Actinidia deliciosa* | Green Kiwi | Fruit | Plants |
| 747 | Act d 2 | *Actinidia deliciosa* | Green Kiwi | Fruit | Plants |
| 2821 | Act d 5 | *Actinidia deliciosa* | Green Kiwi | Fruit | Plants |
| 1279 | Aed c | *Aedes communis* | Biting Insects | Body | Animals |
| 1704 | All c | *Allium cepa* | Onion | Tuber | Plants |
| 1705 | All p | *Allium porrum* | Leek | Tuber | Plants |
| 1706 | All s | *Allium sativum* | Garlic | Tuber | Plants |
| 722 | Alt a 1 | *Alternaria alternata* | *Alternaria alternata* | Spore | Fungi |
| 3063 | Alt a 6.0101 | *Alternaria alternata* | *Alternaria alternata* | Spore | Fungi |
| 6459 | Ama cr | *Amaranthus cruentus* | Blood Amaranth | Seed | Plants |
| 1710 | Amb a | *Ambrosia artemisiifolia* | Mugwort/Ragweed-related Species | Pollen | Plants |

TABLE 1-continued

List of allergens

| Code | Name | Species | Common name | Source | Kingdom |
|---|---|---|---|---|---|
| 24 | *Amb a* 1 | *Ambrosia artemisiifolia* | Mugwort/Ragweed-related Species | Pollen | Plants |
| 694 | *Ana c* 2 | *Ananas comosus* | Pineapple | Fruit | Plants |
| 1714 | *Ana o* [Seed] | *Anacardium occidentale* | Cashew | Seed | Plants |
| 1077 | *Ana o* 3 | *Anacardium occidentale* | Cashew | Seed | Animals |
| 1033 | *Ana p* [Egg White] | *Anas platyrhynchos* | Pistachio | Egg | Plants |
| 10853 | *Ana p* [Egg Yolk] | *Anas platyrhynchos* | Peach | Egg | Plants |
| 2918 | *Ani pe* | *Anisakis pegreffii* | *Anisakis* | Larva | Animals |
| 1716 | *Ani s* | *Anisakis simplex* | *Anisakis* | Larva | Animals |
| 35 | *Ani s* 1 | *Anisakis simplex* | *Anisakis* | Larva | Animals |
| 37 | *Ani s* 3 | *Anisakis simplex* | *Anisakis* | Larva | Animals |
| 8793 | *Api g* [Stalk] | *Apium graveolens* | Celery | Stalk | Plants |
| 41 | *Api g* 1.0101 | *Apium graveolens* | Celery | Root | Plants |
| 1722 | *Api m* [Venom] | *Apis mellifera* | Honey Bee | Venom | Animals |
| 45 | *Api m* 1 | *Apis mellifera* | Honey Bee | Venom | Animals |
| 48 | *Api m* 4 | *Apis mellifera* | Honey Bee | Venom | Animals |
| 11401 | *Ara h* | *Arachis hypogaea* | Peanut | Seed | Plants |
| 11402 | *Ara h* 1-NT | *Arachis hypogaea* | Peanut | Seed | Plants |
| 51 | *Ara h* 2 | *Arachis hypogaea* | Peanut | Seed | Plants |
| 52 | *Ara h* 3 | *Arachis hypogaea* | Peanut | Seed | Plants |
| 55 | *Ara h* 6 | *Arachis hypogaea* | Peanut | Seed | Plants |
| 3100 | *Ara h* 8.0101 | *Arachis hypogaea* | Peanut | Seed | Plants |
| 1050 | *Ara h* Agglutinin | *Arachis hypogaea* | Peanut | Seed | Plants |
| 862 | *Arm r* HRP | *Armoracia rusticana* | Horseradish | Leaf | Plants |
| 1728 | *Art v* | *Artemisia vulgaris* | Mugwort | Pollen | Plants |
| 753 | *Art v* 1 | *Artemisia vulgaris* | Mugwort | Pollen | Plants |
| 1730 | *Asp f* | *Aspergillus fumigatus* | *Aspergillus* | Spore | Fungi |
| 1732 | *Asp n* | *Aspergilus niger* | *Aspergillus* | Spore | Fungi |
| 3050 | *Asp r* 1 | *Aspergillus restrictus* | *Aspergillus* | Spore | Fungi |
| 1734 | *Aspa o* | *Asparagus officinalis* | *Asparagus* | Stem | Plants |
| 1738 | *Ber e* | *Bertholletia excelsa* | Brazil Nut | Seed | Plants |
| 1741 | *Bet v* [Pollen] | *Betula verrucosa* | Birch | Pollen | Plants |
| 90 | *Bet v* 1.0101 | *Betula verrucosa* | Birch | Pollen | Plants |
| 3136 | *Bet v* 2.0101 | *Betula verrucosa* | Birch | Pollen | Plants |
| 2200 | *Beta v* [Leaf] | *Beta vulgaris* | Common Beet | Leaf | Plants |
| 1742 | *Bla g* | *Blattella germanica* | German cockroach | Body | Animals |
| 136 | *Bla g* 1 | *Blattella germanica* | German cockroach | Body | Animals |
| 141 | *Bla g* 2 | *Blattella germanica* | German cockroach | Body | Animals |
| 143 | *Bla g* 4 | *Blattella germanica* | German cockroach | Body | Animals |
| 144 | *Bla g* 5 | *Blattella germanica* | German cockroach | Body | Animals |
| 1744 | *Blo t* | *Blomia tropicalis* | *Blomia* | Body | Animals |
| 2019 | *Bos d* [Meat] | *Bos domesticus* | Cow | Muscle | Animals |
| 10999 | *Bos d* [Milk] | *Bos domesticus* | Cow | Milk | Animals |
| 163 | *Bos d* 4 | *Bos domesticus* | Cow | Milk | Animals |
| 164 | *Bos d* 5 | *Bos domesticus* | Cow | Milk | Animals |
| 165 | *Bos d* 6 | *Bos domesticus* | Cow | Milk | Animals |
| 167 | *Bos d* 8 | *Bos domesticus* | Cow | Milk | Animals |
| 10878 | *Bos d* CA | *Bos domesticus* | Cow | Muscle | Animals |
| 7669 | *Bos d* Gelatin | *Bos domesticus* | Cow | Skin | Animals |
| 1065 | *Bos d* LF | *Bos domesticus* | Cow | Milk | Animals |
| 1755 | *Bub b* [Milk] | *Bubalus bubalis* | Domestic Water Buffalo | Milk | Animals |
| 4043 | *Cam d* [Milk] | *Camelus dromedarius* | Dromedary | Milk | Animals |
| 1756 | *Can f* [Epithelium] | *Canis familiaris* | Dog | Epithelium | Animals |
| 174 | *Can f* 1 | *Canis familiaris* | Dog | Epithelium | Animals |
| 175 | *Can f* 2 | *Canis familiaris* | Dog | Epithelium | Animals |
| 176 | *Can f* 3 | *Canis familiaris* | Dog | Serum | Animals |
| 5762 | *Can f* 5 | *Canis familiaris* | Mites | Epithelium | Animals |

TABLE 1-continued

List of allergens

| Code | Name | Species | Common name | Source | Kingdom |
|---|---|---|---|---|---|
| 1757 | Cand a | Candida albicans | Candida | Spore | Fungi |
| 1760 | Cap h [Milk] | Capra hircus | Goat | Milk | Animals |
| 709 | Car p 1 | Carica papaya | Papaya | Fruit | Plants |
| 1540 | Car p Chymopapain | Carica papaya | Papaya | Fruit | Plants |
| 2025 | Cas s [Seed] | Castanea sativa | Birch/Hazel/Oak-related Species | Seed | Plants |
| 1765 | Cav p [Epithelium] | Cavia porcellus | Guinea Pig | Epithelium | Animals |
| 10907 | Cer si [Seed] | Ceratonia siliqua | Carob | Seed | Plants |
| 2223 | Che qu | Chenopodium quinoa | Quinoa | Seed | Plants |
| 1771 | Cic a | Cicer arietinum | Chickpea | Seed | Plants |
| 2229 | Cit r [Fruit] | Citrus reticulata | Mandarin Orange | Fruit | Plants |
| 1775 | Cla h | Cladosporium herbarum | Fungi | Spore | Fungi |
| 1778 | Cor a [Pollen] | Corylus avellana | Hazelnut | Pollen | Plants |
| 2028 | Cor a [Seed] | Corylus avellana | Hazelnut | Seed | Plants |
| 235 | Cor a 1.0103 | Corylus avellana | Hazelnut | Pollen | Plants |
| 5886 | Cor a 14 | Corylus avellana | Mites | Seed | Animals |
| 245 | Cor a 8 | Corylus avellana | Hazelnut | Seed | Plants |
| 246 | Cor a 9 | Corylus avellana | Hazelnut | Seed | Plants |
| 2429 | Cot c [Egg white] | Coturnix coturnix | Gold Kiwi | Egg | Plants |
| 2430 | Cot c [Egg yolk] | Coturnix coturnix | Gold Kiwi | Egg | Plants |
| 1782 | Cri c | Cricetus cricetus | Hamster | Epithelium | Animals |
| 1784 | Cry j | Cryptomeria japonica | Cedar | Pollen | Plants |
| 1786 | Cuc m [Pulp] | Cucumis melo | Muskmelon | Fruit | Plants |
| 1789 | Cuc s | Cucumis sativus | Cucumber | Fruit | Plants |
| 256 | Cup a 1 | Cupressus arizonica | Arizona Cypress | Pollen | Plants |
| 1799 | Dau c | Daucus carota | Carrot | Root | Plants |
| 295 | Der f 1 | Dermatophagoides farinae | Arizona Cypress | Body | Plants |
| 302 | Der f 2 | Dermatophagoides farinae | Arizona Cypress | Body | Plants |
| 310 | Der p 1 | Dermatophagoides pteronyssinus | Mites | Body | Animals |
| 311 | Der p 10 | Dermatophagoides pteronyssinus | Mites | Body | Animals |
| 316 | Der p 2 | Dermatophagoides pteronyssinus | Mites | Body | Animals |
| 5748 | Der p 23.0101 | Dermatophagoides pteronyssinus | Mites | Body | Animals |
| 321 | Der p 7 | Dermatophagoides pteronyssinus | Mites | Body | Animals |
| 323 | Der p 9 | Dermatophagoides pteronyssinus | Mites | Body | Animals |
| 3995 | Equ as [Milk] | Equus asinus | Donkey | Milk | Animals |
| 1813 | Equ c [Epithelium] | Equus caballus | Horse | Epithelium | Animals |
| 2032 | Equ c [Milk] | Equus caballus | Horse | Milk | Animals |
| 335 | Equ c 3 | Equus caballus | Horse | Serum | Animals |
| 10877 | Equ c Myoglobin | Equus caballus | Horse | Muscle | Animals |
| 340 | Eur m 2 | Euroglyphus maynei | Horse | Body | Animals |
| 1816 | Fag e | Fagopyrum esculentum | Horse | Seed | Animals |
| 1819 | Fel d | Felis domesticus | Cat | Epithelium | Animals |
| 345 | Fel d 1 | Felis domesticus | Cat | Epithelium | Animals |
| 346 | Fel d 2 | Felis domesticus | Cat | Serum | Animals |
| 2034 | Foe v [Bulb] | Foeniculum vulgare | Fennel | Bulb | Plants |
| 1826 | Fra a [Fruit] | Fragaria ananassa | Strawberry | Fruit | Plants |
| 1831 | Gad m [Meat] | Gadus morhua | Atlantic Cod | Muscle | Animals |
| 1832 | Gal d [Egg White] | Gallus domesticus | Chicken | Egg | Animals |
| 2036 | Gal d [Egg Yolk] | Gallus domesticus | Chicken | Egg | Animals |
| 2037 | Gal d [Meat] | Gallus domesticus | Chicken | Muscle | Animals |
| 359 | Gal d 1 | Gallus domesticus | Chicken | Egg | Animals |
| 360 | Gal d 2 | Gallus domesticus | Chicken | Egg | Animals |
| 361 | Gal d 3 | Gallus domesticus | Chicken | Egg | Animals |

TABLE 1-continued

List of allergens

| Code | Name | Species | Common name | Source | Kingdom |
|---|---|---|---|---|---|
| 362 | Gal d 4 | Gallus domesticus | Chicken | Egg | Animals |
| 363 | Gal d 5 | Gallus domesticus | Chicken | Egg | Animals |
| 1834 | Gly m | Glycine max | Soy | Seed | Plants |
| 368 | Gly m 1 | Glycine max | Soy | Seed | Plants |
| 1429 | Gly m Agglutinin | Glycine max | Soy | Seed | Plants |
| 1144 | Gly m Tl | Glycine max | Soy | Seed | Plants |
| 1840 | Hel as | Helix aspersa | Brown Garden Snail | Muscle | Animals |
| 378 | Hel as 1 | Helix aspersa | Brown Garden Snail | Muscle | Animals |
| 1841 | Hev b | Hevea brasiliensis | Latex | Latex | Plants |
| 379 | Hev b 1 | Hevea brasiliensis | Latex | Latex | Plants |
| 380 | Hev b 10 | Hevea brasiliensis | Latex | Latex | Plants |
| 384 | Hev b 11 | Hevea brasiliensis | Latex | Latex | Plants |
| 3314 | Hev b 3.0101 | Hevea brasiliensis | Latex | Latex | Plants |
| 3316 | Hev b 5.0101 | Hevea brasiliensis | Latex | Latex | Plants |
| 392 | Hev b 6.02 | Hevea brasiliensis | Latex | Latex | Plants |
| 396 | Hev b 7.02 | Hevea brasiliensis | Latex | Latex | Plants |
| 397 | Hev b 8 | Hevea brasiliensis | Latex | Latex | Plants |
| 404 | Hev b 9 | Hevea brasiliensis | Latex | Latex | Plants |
| 763 | Hom s HSA | Homo sapiens | Humans | Serum | Animals |
| 1384 | Hom s LF | Homo sapiens | Humans | Milk | Animals |
| 2040 | Hor v [Seed] | Hordeum vulgare | Barley | Seed | Plants |
| 1850 | Jug r [Seed] | Juglans regia | Walnut | Seed | Plants |
| 425 | Jug r 2 | Juglans regia | Latex | Seed | Plants |
| 426 | Jug r 3 | Juglans regia | Walnut | Seed | Plants |
| 1856 | Lac s | Lactuca sativa | Mugwort/Ragweed-related Species | Leaf | Plants |
| 1857 | Len c | Lens culinaris | Lentil | Seed | Plants |
| 905 | Lin us | Linum usitatissimum | Linum usitatissimum | Seed | Plants |
| 1868 | Lol p [Pollen] | Lolium perenne | Grasses | Pollen | Plants |
| 450 | Lol p 1 | Lolium perenne | Gr | Pollen | Plants |
| 940 | Lup a [Seed] | Lupinus albus | Lupinus albus | Seed | Plants |
| 1871 | Mal d [Fruit] | Malus domestica | Malus domestica | Fruit | Plants |
| 1454 | Mal d 1.0108 | Malus domestica | Malus domestica | Fruit | Plants |
| 1035 | Mel g [Egg white] | Meleagris gallopavo | Common Turkey | Egg | Animals |
| 10909 | Mel g [Egg yolk] | Meleagris gallopavo | Common Turkey | Egg | Animals |
| 2049 | Mel g [Meat] | Meleagris gallopavo | Common Turkey | Muscle | Animals |
| 476 | Mer a 1 | Mercurialis annua | Mercurialis annua | Muscle | Plants |
| 7643 | Mer mr 1 | Merluccius merluccius | European Hake | Muscle | Animals |
| 2051 | Mus m [Epithelium] | Mus musculus | Mouse | Epithelium | Animals |
| 478 | Mus m 1 | Mus musculus | Mouse | Epithelium | Animals |
| 755 | Mus m 4 | Mus musculus | Mugwort | Serum | Plants |
| 1413 | Myt e | Mytilus edulis | Blue Mussel | Muscle | Animals |
| 2132 | Oct v | Octopus vulgaris | Octopus | Muscle | Animals |
| 1888 | Ole e [Pollen] | Olea europaea | Olive Tree | Pollen | Plants |
| 482 | Ole e 1 | Olea europaea | Olive Tree | Pollen | Plants |
| 490 | Ole e 2 | Olea europaea | Olive Tree | Pollen | Plants |
| 2054 | Ory c [Epithelium] | Oryctolagus cuniculus | Mouse | Epithelium | Animals |
| 2057 | Ory c [Meat] | Oryctolagus cuniculus | Rabbit | Muscle | Animals |
| 759 | Ory c 6 | Oryctolagus cuniculus | Rabbit | Serum | Animals |
| 11394 | Ory s [Seed] | Oryza sativa | Oryza sativa | Seed | Plants |
| 2061 | Ovi a [Meat] | Ovis aries | Sheep | Muscle | Animals |
| 1892 | Ovi a [Milk] | Ovis aries | Sheep | Milk | Animals |
| 758 | Ovi a 6 | Ovis aries | Sheep | Serum | Animals |
| 1893 | Pan b | Pandalus borealis | Crustaceans | Muscle | Animals |
| 1904 | Par j | Parietaria judaica | Pellitory | Pollen | Plants |
| 507 | Par j 2 | Parietaria judaica | Pellitory | Pollen | Plants |
| 1912 | Pen ch | Penicillium chrysogenum | Penicillium | Spore | Fungi |
| 972 | Pen m 1 | Penaeus monodon | Black Tiger Prawn | Muscle | Animals |
| 1917 | Per a | Periplaneta americana | American Cockroach | Body | Animals |
| 542 | Per a 7 | Periplaneta americana | American Cockroach | Muscle | Animals |

TABLE 1-continued

List of allergens

| Code | Name | Species | Common name | Source | Kingdom |
|---|---|---|---|---|---|
| 1920 | *Pers a* | *Persea americana* | *Persea americana* | Fruit | Plants |
| 1923 | *Pha v* [Seed] | *Phaseolus vulgaris* | Legumes | Seed | Plants |
| 1924 | *Phl p* | *Phleum pratense* | Grasses | Pollen | Plants |
| 551 | *Phl p* 1.0102 | *Phleum pratense* | Grasses | Pollen | Plants |
| 3419 | *Phl p* 2.0101 | *Phleum pratense* | Grasses | Pollen | Plants |
| 559 | *Phl p* 5.0101 | *Phleum pratense* | Grasses | Pollen | Plants |
| 3420 | *Phl p* 6.0101 | *Phleum pratense* | Grasses | Pollen | Plants |
| 3422 | *Phl p* 7.0101 | *Phleum pratense* | Grasses | Pollen | Plants |
| 714 | *Pin p* [Seed] | *Pinus pinea* | Pine tree | Seed | Plants |
| 1008 | *Pis v* [Seed] | *Pistacia vera* | Pistachio | Seed | Plants |
| 1932 | *Pla a* | *Platanus acerifolia* | Sycamore tree | Pollen | Plants |
| 572 | *Pla a* 1 | *Platanus acerifolia* | Sycamore tree | Pollen | Plants |
| 10875 | *Ple o* [Sporocarp] | *Pleurotus ostreatus* | Mushrooms | Sporocarp | Fungi |
| 2322 | *Pol* spp | *Polistes* spp | Hymenoptera | Venom | Animals |
| 1945 | *Pru ar* [Fruit] | *Prunus armeniaca* | Cherry | Fruit | Plants |
| 1948 | *Pru du* [Seed] | *Prunus dulcis* | Almond Tree | Seed | Plants |
| 2070 | *Pru p* [Peel] | *Prunus persica* | Peach | Fruit | Plants |
| 2069 | *Pru p* [Pulp] | *Prunus persica* | Peach | Fruit | Plants |
| 603 | *Pru p* 3 | *Prunus persica* | Peach | Fruit | Plants |
| 9147 | *Pru p* 7 | *Prunus persica* | Peach | Fruit | Plants |
| 1195 | *Pun g* | *Punica granatum* | Pomegranate | Fruit | Plants |
| 2834 | *Pun g* 1 | *Punica granatum* | Pomegranate | Fruit | Plants |
| 11786 | *Pun g* 14 | *Punica granatum* | Pomegranate | Fruit | Plants |
| 11787 | *Pun g* 5 | *Punica granatum* | Pomegranate | Fruit | Plants |
| 11614 | *Pun g* 7 | *Punica granatum* | Pomegranate | Fruit | Plants |
| 1955 | *Que a* [Pollen] | *Quercus alba* | Plants | Pollen | Plants |
| 2072 | *Rat n* [Epithelium] | *Rattus norvegicus* | Rat | Epithelium | Animals |
| 611 | *Rat n* 1 | *Rattus norvegicus* | Rat | Epithelium | Animals |
| 756 | *Rat n* 4 | *Rattus norvegicus* | Rat | Serum | Animals |
| 1960 | *Sac c* | *Saccharomyces cerevisiae* | Yeast | Spore | Fungi |
| 3348 | *Sal k* 1 | *Salsola kali* | Russian-thistle | Pollen | Plants |
| 1962 | *Sal s* [Meat] | *Salmo salar* | Atlantic Salmon | Muscle | Animals |
| 2363 | *Sar m* | *Sardinops melanostictus* | Fishes | Muscle | Animals |
| 1971 | *Ses i* | *Sesamum indicum* | Sesame | Seed | Plants |
| 1972 | *Sin a* [Seed] | *Sinapis alba* | *Sinapis alba* | Seed | Plants |
| 2368 | *Sol so* | *Solea solea* | Common Sole | Muscle | Animals |
| 1870 | *Sola l* [Fruit] | *Solanum lycopersicum* | Tomato | Fruit | Plants |
| 6131 | *Sola l* [Seed] | *Solanum lycopersicum* | Tomato | Seed | Plants |
| 8215 | *Sola l* 6 | *Solanum lycopersicum* | Tomato | Fruit | Plants |
| 875 | *Sola m* | *Solanum melongena* | Aubergine | Fruit | Plants |
| 1977 | *Sola t* | *Solanum tuberosum* | Potato | Tuber | Plants |
| 639 | *Sola t* 1 | *Solanum tuberosum* | Potato | Tuber | Plants |
| 1980 | *Spi o* | *Spinacia oleracea* | Spinach | Leaf | Plants |
| 2088 | *Sus s* [Meat] | *Sus scrofa domestica* | Pig | Muscle | Animals |
| 757 | *Sus s* 1 | *Sus scrofa domestica* | Pig | Serum | Animals |
| 2375 | *Thu a* [Meat] | *Thunnus albacares* | Fishes | Muscle | Animals |
| 11396 | *Tri a* [Seed] | *Triticum aestivum* | Wheat | Seed | Plants |
| 8724 | *Tri a* 7k-LTP | *Triticum aestivum* | Wheat | Seed | Plants |
| 650 | *Tri a* 18 | *Triticum aestivum* | Wheat | Seed | Plants |
| 8186 | *Tri a* 28 | *Triticum aestivum* | Wheat | Seed | Plants |
| 651 | *Tri a* Gliadin | *Triticum aestivum* | Wheat | Seed | Plants |
| 2653 | *Tri me* | *Trichophyton mentagrophytes* | Fungi | Whole body | Fungi |
| 921 | *Tri tp* | *Triticum polonicum* | Grasses | Seed | Plants |
| 8169 | *Uro du* | *Uroteuthis duvauceli* | Indian Squid | Muscle | Animals |
| 11791 | *Uro du* 1 | *Uroteuthis duvauceli* | Indian Squid | Muscle | Animals |
| 6340 | *Ven ga* | *Venus gallina* | Clam | Muscle | Animals |
| 11788 | *Ven ga* 1 | *Venus gallina* | Clam | Muscle | Animals |
| 2400 | *Ves* spp | *Vespula* spp | Hymenoptera | Venom | Animals |
| 2012 | *Vit v* [Fruit] | *Vitis vinifera* | Grape | Fruit | Plants |

TABLE 1-continued

List of allergens

| Code | Name | Species | Common name | Source | Kingdom |
|---|---|---|---|---|---|
| 11392 | Zea m [Seed] | Zea mays | Corn | Seed | Plants |
| 684 | Zea m 14 | Zea mays | Corn | Seed | Plants |

Infection markers are substances, compositions or particles which are indicative for the presence of an infectious agent such as viruses, parasites, bacteria, prions and fungi.

Infection markers include, but are not limited to proteins, glycoproteins (e.g surface or coat proteins of bacteria or viruses), mixtures of proteins (e.g. bacterial cell lysate), other detectable compounds associated with an infectious agent or particles (e.g., virus-like particles or viral coat proteins, bacterial surface antigens, etc.).

Autoantigens are molecules created by an organism, such as a human, for which there is an immune response by that organism such as the generation of antibodies to the autoantigen, i.e. generation of an autoantibody. The production of autoantibodies is generally associated with autoimmune disease. Examples of autoantigens include both organ-specific antigens such as thyroglobulin and ubiquitous cellular antigens such as DNA, histones, and ribonucleoprotein particles. Exemplary autoantigens that may be included in the antigen array described herein are listed in Table 2.

TABLE 2

Autoantigens

| Protein | Disease | Protein | Disease |
|---|---|---|---|
| SmB/SmB' | SLE | RuvB-like 1 | PM, Der, AH |
| Sm-D1 | SLE | CHD-3 | Der |
| Sm-D2 | SLE | CHD-4 | Der |
| Sm-D3 | SLE | RCC1 | Ray |
| U1 snRNP A | SLE | PM/Scl-100, PM/Scl-2 | PM, SScl |
| U1 snRNP 70K | SLE | PM/Scl-75, PM/Scl-1 | PM, SScl |
| U1 snRNP C | SLE | RRP42 | PM, SScl |
| U2 snRNP A' | SLE | RRP4 | PM, SScl |
| U2 snRNP B" | SLE | Fibrillarin | SScl, in 8% patients |
| Ro52K SS-A1 | SLE, SS | UBF-1 | SScl, Autoantigen NOR-90 |
| Ro60K SS-A2 | SLE, SS | PA28g | SLE |
| La SS-B | SLE, SS | SSNA1 | SS |
| Histone H1b | SLE | hnRNP A/B | SLE, RA, MCTD |
| Histone H2A.1b | SLE | hnRNP A2 | SLE, RA, MCTD |
| Histone H2B.1a | SLE | ZNF330 | RA, Nucleolar autoantigen 36 |
| Histone H3.1 | SLE | ASF-1 SRp30a | SLE |
| Histone H4 | SLE | SC35 SRp30b | SLE |
| DNA topoisomerase I | SScl (retroviral p30gag) | SRp20 | SLE |
| CENP-A | Ray, Crest (SScl sub) | SRp75 | SLE |
| CENP-B | Ray, Crest (SScl sub) | SRp40 | SLE |
| CENP-C | SS, SScl, autoantigen | SRp55 | SLE |
| Ku86 | SLE | DBP1 | SScl, SLE |
| Ku70 | SLE, Cterm 190 residues | NUMA1 | SS |
| Annexin A11 | SLE, SS, RA | Eg5Kinesin-likeNUMA-2 | SS, SLE |

TABLE 2-continued

Autoantigens

| Protein | Disease | Protein | Disease |
|---|---|---|---|
| RNaseP p38 | SScl, 4/4 sera | PCNA (cyclin) | SLE sera contains PCNA |
| RNaseP p30 | SScl, 2/4 sera | CCP | RA |
| Fibrinogen | RA | Rheumatoid factor | RA, SLE |
| Ro52 | RA | Collagen | RA |

Disease Abbreviation:
SLE = Systemic Lupus Erythematosus
SS = Sjogren Syndrome
SScl = Scleroderma (Systemic Sclerosis)
PM = Polymyositis
Der = Dermatomyositis
Ray = Raynaud disease,
RA = Rheumatoid Arthritis
MCTD = Mixed Connective Tissue Disease The antigens, i.e. detection antigens, of the antigen array described herein may be antigens produced by recombinant DNA technology, or antigens purified and isolated from a biological source material (e.g., antigens from a biological material substantially free of any other antigens, which can be isolated from the same biological material by methods known in the art (compare Ian R. Mackay & Noel R. Rose, The Autoimmune Diseases, Fifth Edition, Academic Press 2014). In some embodiments, the beads are coupled with a recombinantly produced antigen. In some embodiments, the beads are coupled with an isolated and purified detection antigen from a biological source.

In some embodiments, the antigen array comprises groups of beads with a set of detection antigens (e.g., at least one, two or more detection antigens). For example, the set of detection antigens may be obtained from an extract (e.g. an allergen extract) or lysate (e.g. a bacterial lysate or other cell lysate) of a biological source. In some embodiments, the beads are coupled with an extract or lysate of a biological source, thereby producing antigen-coated beads with a set of detection antigens.

In some embodiments, the beads are coated with a molecular allergen produced by recombinant DNA technology. In some embodiments, the beads are coated with an allergen isolated or purified from a biological source. In some embodiments the beads are coated with an allergen extract (e.g. a set of allergens such as at least one, two or more allergens from a biological material). The allergen extract may comprise a raw allergen extract; a concentrated allergen extract; or several allergens purified from an allergen extract. The allergens are naturally occurring allergens. An allergenic extract may naturally contain one or more isoforms of the same allergen. The allergen extract can also consist of a mixture of at least two allergen extracts of different biological sources, e.g. two different but closely related species of a similar basic origin, usually referred to as spp.

Antigen Coupling Using Micro- or Nano-Particles

The antigen array described herein employs a principle of individualized optimized coupling strategy of heterogeneous and complex biological antigens (i.e., detection antigens). In a multiplexed immunological antibody detection assay, this is a prerequisite to achieve the optimal test performance for each single parameter.

The antigen coupling proceeds in two distinct steps. In the first step, each antigen is coupled to a micrometer or nanometer scale suspended particles, e.g., a microbead or nanobead.

In a specific embodiment, those particles are spherical particles which can be kept in solution in aqueous buffers such as those typically used for protein or more generally biomolecule storage. Particles can be latex or polystyrene particles, plastic polymeric particles or particles made from glass (silica), porous or non-porous surface particles, or even particles made from other biocompatible polymers. The size of the particles can be between a few nanometers up to a micron, whereby the preferred size of the particles is between 5 and 500 nm in diameter, more preferably between 200 and 500 nm, even more preferably between 200 and 350 nm (e.g. about 350 nm) in diameter. In some embodiments, the beads are polystyrene nanoparticles.

The attachment of the antigens (proteins, peptides, antibodies, DNA and other biomolecules made of nucleic acids, amino acids or organic or non-organic chemical compounds, which can serve as antigens) can proceed via various attachment strategies.

In the simplest embodiment the antigenic molecule or macromolecule will attach to the particle (bead) by passive adsorption, for example hydrophobic and/or electrostatic attachment. The attachment can be facilitated by choosing the appropriate buffer system, which creates the environment for the maximum attachment, for example by choosing a buffer system which has a pH value close to the isoelectric point of the antigen thereby neutralizing the surface charge in average.

In a more complex setup, the antigen to be coupled consists of either various single antigen bearing molecules or a single macromolecule with several antibody binding epitopes or even a complex mixture of various proteins with individually different antigens containing a variety of epitopes (e.g. an extract or lysate of a biological source material comprising a set of detection antigens), which might require different adsorption conditions in order to achieve optimal biological binding capabilities (avidity). In such case, the antigen or antigen mixture can be split into several aliquots, and each aliquot coupled under different conditions, for example different pH values or different ionic buffer strength or different buffer additives such as salt, detergents, buffer substances etc. Under each condition, each antigen couples in a certain configuration which might be preferable for biological activity, or a fraction of certain antigens might couple more easily than another subpopulation, or not at all under the conditions chosen. In following step, the different aliquots can be reunited in order to create a population of micro- or nanoparticles which carry different antigens from the initial complex mixture, or a single antigen in various structural configurations. By achieving this, the original epitope repertoire of the biological sample can be coupled to the particles without creating a bias in a way that only selected epitopes are preserved, or that only selected antigen carriers from a complex mixture are actually coupled.

By choosing a sufficient number of different coupling conditions and optimizing the mixture of the differentially coupled particle-antigen combinations, the final particle solution charged with antigens will assemble closely the epitope repertoire of the original mixture, or it is possible to enrich preferable antigen carriers in the particle solution in that way while still maintaining the complete epitope complexity in total.

In an even more sophisticated setup, the antigens can be coupled by employing a plethora of combinatorial organic coupling chemistry known to those skilled in the art. By this strategy, antigens can be coupled covalently to the particles and it is possible to selectively couple to a certain chemical group present on the surface of the antigens, for example an amino or carboxyl group, a sulfhydryl group, an aromatic residue etc.

It is further possible to use suitable antigen spacers in order to optimize antigen presentation when working with small antigens such as peptides or chemical compounds.

By chemical surface engineering of the particle surface it is further possible to optimize the coupling of the beads to the solid carrier surface, suppress unspecific binding or enhance antibody binding.

In some embodiments, the detection antigen or set of detection antigen are covalently bound to the beads (e.g. via an EGS linker to NH2 surface beads, via an EDC linker to COOH surface beads). In some embodiments, the detection antigen or set of detection antigens are non-covalently bound to the beads. For example, the beads can be coated with an antigen or set of detection antigen by passive adsorption.

It is further possible to optimize particle size to fit the requirements of the manufacturing process. The particles shall be easy to handle and keep in solution, and at the same time they shall attach specifically or non-specifically once deposited to the final solid support. After charging the particles with antigens, the charged particles can be separated from the remaining antigen solution, for example by centrifugation, magnetic separation, electric charge or size exclusion, among others. By this separation it is possible to maintain only the fraction of preferably coupled antigens and get rid of the remaining, probably non-antigenic fraction of the original antigen mixture.

Functional testing of the antigen-coupled particles may be performed and the results compared against available reference tests performed with a reference in vitro diagnostic method, against clinical reference data, or against available standard preparations. Since there is no internationally recognized laboratory standard for more than very few antigen specific IgE antibodies, one available reference system is the Biorad Lyphocheck® quality control samples which have been tested for IgE against the major allergens on the three most widely used automatic immunoassay instruments (www.bio-rad.com).

The extent of antigen coupling can be checked by various methods known in the art. For example, the supernatant from the coupling reaction can be used for an ELISA assay, can be measured for protein content, or can be tested on a 1D or 2D protein gel, whereby not only the total content of not coupled antigens can be estimated, but also the nature of the unbound as well as bound antigen carriers (those which are no longer present on the gel) can be documented by looking at the size/position of the protein peaks or dots. If required, the supernatant can further be analyzed by mass spectrometry.

A similar approach can be applied for testing the stability of the coupling. For example, by coupling the particles and then testing the supernatant (non-particle containing solution) after defined time intervals, it can be determined if antigenic proteins stay permanently attached to the particles or if they diffuse back into solution after a certain amount of time or under certain conditions of storage, with certain storage buffers or detergents.

Storage of Antigen Coupled Beads and Handling Thereof During Manufacturing

The storage of the coupled beads can proceed under conditions which stabilize the protein bound to the particles for at least several months, preferable several years after the initial coupling, with the two main goals of firstly, keeping the proteins attached to the particles, secondly and more importantly keeping the proteins biologically active and protect them from degradation, e.g. by proteolytic digestion. Also, the beads have to be kept in solution and any precipitation has to be avoided, as this could lead to aggregate formation which cannot be dissolved afterwards, thereby blocking or destroying part of the epitope repertoire present in the original antigen solution, without using harsher and potentially antigen damaging methods (heat, shearing, sonication, vortexing etc.).

The above approach presents a significant improvement for any immune assay manufacturing process given that the reagents can be stabilized sufficiently for a longer period or even indefinitely when stored at for example −80° C. The advantage of having stable primary reagent sets for the subsequent manufacturing process is mainly that once a good reagent is produced, assuming that it is stable for a long time, relatively little effort needs to be put in quality control procedures. Whereas if the coupling would have to be done fresh in shorter intervals, each time the coupling is complete a full set of quality control measures and documentation has to be filed. There would still be a remaining uncertainty whether the variation stems from the coupling process or the previous deterioration of the antigen solution, which might be more difficult to store for longer time than they actually adsorbed antigens on the surface of the particles. It is known to those skilled in the art that proteins cannot be stored indefinitely in a simple solution, even at low temperatures, mainly because repeated freezing and thawing can deteriorate the quality and proteins have a tendency to precipitate or attach to each other. The stability however of surface attached proteins can be significantly longer even under less favorable storage conditions.

The conditions under which storage for a longer period is possible also include choosing the best temperature range, normally either −20° C. or a range between 2-8° C., preferably 2-4° C.

The buffers applicable for storage for antigen-coated beads as described herein include but are not limited to: Simple NaCl solution, Phosphate buffers, Tris buffer, MES buffer, Citrate buffer, HEPES buffer etc.

The pH conditions for storage are preferable in a physiological range, between pH 7-8, but can also be in a range between ph 6-9 or even between pH 2-14.

The additives for allowing longer storage include but are not limited to: Non-ionic detergents, such as Tween-20, SDS, Triton, others.

Sodium azide, kathon or other preservatives can be used to avoid bacterial or fungal growth in the preparations during storage.

Polyalcohols such as glycerol, polyvinyl alcohol etc can be used to stabilize both particles in solution and proteins on the particles.

Polysaccharides such as Trehalose, Saccharose etc can further stabilize the proteins in particular from structural degradation.

Sugars can further be used for protein stabilization even after the particles are coupled to the solid phase of the final assay.

Surface Deposition of Antigen Charged Beads in an Array Format

The transfer of beads from solution to the solid phase can be achieved by several methods known to those skilled in the art. The goal is to transfer a range of individual antigen containing particle solutions (groups of beads) into an ordered array of addressable elements (separate molecular entities with a defined location on the array), so that after incubation with an antigen containing biological sample, e.g. a patient serum, and appropriate detection of the binding event, a detected signal can be associated to respective antigenic source material.

The principle methods for deposition of liquids from a solution onto a solid support are contact or non-contact driven. For contact methods, typically a stamp or pin of some sort dips into a source liquid repeatedly, and in between dipping into the source liquid the gathered material which absorbs to the stamp or pin is deposited onto a solid suppot. This method, being the simpler alternative, however has significant drawbacks when it comes to scalability and reproducibility, as much of the process performance will depend on the nature of the stamp and the source liquid, as well as the wettability of the solid phase, viscosity, composition of the liquid etc.

Therefore, in most modern applications non-contact methods are preferred. For the arrays described herein, a solenoid dispensing system can be used, whereby a syringe creates pressure in a liquid channel containing the antigenic source solution and the precisely timed opening of a solenoid valve allows the formation of precisely uniform droplets out of a ceramic tip. The drop is then ejected from the ceramit tip and after a short flight phase lands and gets attached to the solid phase. The movement of the solid phase under the ceramic tip (or reversely the movement of the tip by motorized axis) allows production of distinct arrays when one after another different source liquid are deposited in an orderly way. Alternatively, the deposition of drops can proceed via the piezo driven drop formation, whereby the main difference to the previously described method is that the pressure is not built by a syringe but by an electric impulse to the piezo crystal, and the dispensed volume is typically much smaller, in the picoliter range, whereas solenoid dispensing works best in the nanoliter range of drops.

The preferable size of the formed droplets is 1 mm in diameter, resulting in circular features (separated molecular entities as addressable elements) on the solid phase of close to 1 mm in diameter. Using such dimensions, it is possible to create arrays of roughly 10×10 (100 in total) different antigen coupled areas per square centimeter. The amount of liquid dispensed in such way to the solid phase is around 30 nl per drop, but can be between 1 nanoliter and 200 nanoliter, or even higher. The circular features or units comprising a specific group of antigen-coated beads can be identified by their location/position (are spatially addressable) and can be arranged in a regular rectangular array or an orange packed array. The arrays described herein have 1 to 9 addressable elements per $mm^2$, e.g., any one of 1, 2, 3, 4, 5, 6, 7, 8, or 9 addressable elements per $mm^2$.

Important variables for the quality of the deposited spots (homogeneity, shape, position tolerance etc) and quantitative reproducibility in terms of variation coefficient of final measurement are: distance from target, pressure in the channel; open times of the vales; drop volume; movement speed of axis; time between dispense; ceramic tip in process and in-between process cleaning and conditioning; pre-spotting routine before actual spot deposition process; aspiration volume and aspiration speed; and microtiter plate geometry. During the deposition process, it is required to keep the antigen coupled particles in solution when inside the liquid handling equipment, and avoid any cross-contamination in between the deposition of different antigen-coated beads by sufficient cleaning of the liquid channels in between aspiration and dispensing cycles.

In order to achieve zero-defect deposition process, it is important to detect every single dispense defect event, for example, by adding a non-permanent color to the particle solution, which allows to detect the successful deposition of the liquid to the solid phase, but will wash out during the actual testing procedure. In that way, a missing drop can be detected and retrospectively added after the initial dispensing round, thereby leading to 100% complete batches in 100% of the time.

Solid Support

The deposition process is normally done on larger sheets or plates of the solid support material, whereby each batch typically consists of several hundreds to several thousands of identical arrays. A continuous process can be realized by aligning the required number of dispense channels and moving a substrate on plates or even a reel to reel system below the dispense tips, and timing the positioning and dispense event so that orderly arrays of particle spots are created on the solid support.

After the dispensing step, the solid support is cut into appropriately sized pieces, for further assembly or storage. Alternatively, the solid support can be cut to suitable sizes even before the deposition of the antigen-coated beads, where the size of the pieces corresponds to the number of groups of particles deposited and the density of the individual groups. In a preferred embodiment, the individual pieces of solid support are rectangular and between 5×5 mm and 200×200 mm or larger, even more preferably between 10×10 and 20×30 mm.

A solid support may be composed of nitrocellulose, laminated nitrocellulose or diazo paper or organic polymers such as polystyrene, polyethylene, polypropylene, polyfluoroethylene, polyethyleneoxy, polyvinylidene difluoride (PVDF), polyacrylamide, polycarbonate, polyallomer, polyvinyl, nylon, as well as co-polymers and grafts thereof or other functionalized plastics. A solid support may also be inorganic, such as glass, silica, controlled-pore-glass (CPG), or reverse-phase silica. The configuration of a solid support may be in the form of a membrane or a surface, and may be planar, substantially planar, or non-planar. Solid supports may be porous or non-porous, and may have swelling or non-swelling characteristics.

The nature of the solid support can be a porous or non-porous material, with the ability to retain particles charged with protein antigens. For example, nitrocellulose sheets or laminated nitrocellulose sheets can be used as solid phase, whereby the pore size and exact composition of the nitrocellulose can have significant effect on the performance of the test. Even chemical activation of the nitrocellulose in order to be able to covalently bind biomolecules could have a beneficial effect on the test results. Different types of nitrocellulose membranes are available as solid support, such nitrocellulose membranes differ regarding pore size, flow rates or base material. Preferably, the pore size shall be in the range of the particle size, so that the particles can be retained by the pores on the surface, but at the same time do not disappear within the structure of the solid support, which would make it more difficult for the antibody to bind to the surface of the particles.

The solid phase shall be durable and compatible with a typical ELISA procedure which requires several hours of incubation and washing in aqueous solutions. Non-specific binding to the surface shall be either intrinsically low, or it must be possible to block any non-specific binding to the solid phase in order to achieve the required signal to noise ratio (signal divided by noise standard deviation).

Storage of Tests and Assembly into Cartridge

In order to stabilize the particles after deposition to the solid support, the solid support can be stored at appropriate temperature, preferably 2-8° C. In addition, sugar or other stabilizing substances can be added by spray coating after the particle deposition. The requirement for stability is at least one year after manufacturing, preferably at least 30 months after manufacturing, which would leave 6 months for shipping to end user after manufacturing and a remaining shelf life of 24 months at the end user.

For practical handling, storage and shipping as well as kit packaging purposes, the cut strips of the solid support will be assembled into a cartridge which is described in more detail below. The cartridge not only provides physical protection for the solid support macro arrays, but also provides a highly sophisticated and functional container which greatly facilitates the automatic processing of the tests, the liquid handling and disposal of potentially contaminated materials.

Assay Procedure

Further described herein are in vitro methods of detecting an immunoglobulin specific for a detection antigen or for a set of detection antigens using the antigen array described herein. Specifically, the method comprises (i) Providing an antigen array as described herein,
(ii) Incubating the array with a sample,
(iii) Incubating the array with a detection reagent,
(iv) Optionally, incubating the array with a signal generation reagent, and
(v) Measuring a detectable signal.

An increased detectable signal compared to a negative control signal indicates presence of the immunoglobulin in the sample, while no signal increase indicates absence of the immunoglobulin in the sample.

In some embodiments, the detectable signal is a colorimetric, fluorescent, electrical or chemiluminescent signal.

The biological assay as described herein has the purpose of detecting specific immunoglobulins against a plurality of antigens in a single analytical procedure which is based on the ELISA principle and usually consists of the following basic steps:

1) Pre-Washing
2) Blocking
3) Incubation with sample
4) Washing
5) Incubation with detection reagent
6) Washing
7) Optional: Incubation with signal generation
8) Optional: Stopping signal generation
9) Detection and measurement of result In some embodiments, the methods of detecting an immunoglobulin specific for a detection antigen or a set of detection antigens (e.g. an allergen or set of allergens) using the antigen array described herein comprises (i) Providing an antigen array (e.g. an allergen array) as described herein, (ii) Incubating the array with a sample (e.g. serum or whole or processed blood),
(iii) Incubating the array with a detection reagent (e.g. an anti-IgE or anti-IgG antibody or an IgE-specific or IgG-specific aptamer directly labeled with a detectable signal, an anti-IgE or IgG antibody or an IgE-specific or IgG-specific aptamer conjugated to an enzyme)
(iv) Optionally, incubating the array with a signal generation reagent (e.g., a substrate for the enzymatic reaction),
(v) Optionally adding a stop solution to end signal generation, and
(vi) Measuring a detectable signal.

A sample in that respect can be a patient serum, whole or processed blood, nasal fluid, urine, other bodily fluids or cell lysates or homogenates from tissues etc. The sample can be from a single subject or from a pool of subjects (e.g. pool of serum of 10, 20, 30 subjects when screening a large population of subjects). In some embodiments, the sample is a blood sample (e.g. a serum sample). In some embodiments, the sample size is any one of 1 μl-2000 ul, for example any one of 1 μl to 10 μl, 10 μl to 50 μl, 50 μl to 100 μl, 100 μl to 500 μl, 500 μl to 2000 μl. In some embodiments, the sample size is any one of 1 μl, 2 μl, 3 μl, 4 μl, 5 μl, 10 μl, 20 μl, 50 μl, 100 μl, 250 μl, 500 μl or 1000 μl or 2000 μl. In some embodiments, the sample is undiluted. In some embodiments, the sample is diluted. In some embodiments, the sample dilution is between 1:1 to 1:10, 1:10 to 1:100, between 1:100 to 1:1000 or between 1:1000 to 1:10000. In some embodiments, the sample dilution is any one of 1:10, 1:100, 1:1000 or 1:10000. The actual amount of sample needed can depend on the sample dilution used for the incubation reaction.

The performance of the test shall not be influenced significantly by the biological sample even if the sample is not in perfect condition, which happens frequently during routine blood drawing. Typical problems can be lipemic, hemolytic or icteric sample fluids, samples with high protein content or even high antibody content (IgG, IgE, others).

The detection reagent is an affinity binder of biological origin, preferably an antibody (e.g. detection antibody) either from immunization or artificial selection via a random library. Other affinity binders can be protein or nucleic acid artificially selected binders, such as aptamers or affibodies.

The initial washing step has the purpose of removing any non-permanently bound particles from the solid phase which would otherwise compete with the binding of solid phase bound antigen and free soluble antigen in the sample incubation step.

In general terms, the washing step is not a single step but usually carried out repeatedly, in order to achieve a final deletion of any unwanted reagent below the limit of detection. Specifically, the use of washing steps can be repeated 3-5 times, whereby a dilution of the volume is assumed by tilting the cartridge and adding fresh wash solution is at least 30 fold, so that after 3 rounds of washing the dilution is approx. 1 in 27.000, any additional washing step would even further increase the dilution by a factor of 30.

The blocking step is intended to block any possibility of unspecific binding of either constituents of the sample, such as the antibody to be detected but not specific for an immobilized antigen, as well as the unspecific binding of the detection reagent.

The blocking can be done once before the incubation with sample, or can be done repeatedly before every step of the assay, or the blocking reagent can be added to dilute the sample to be measured or even the detection reagent (e.g. the detection antibody, aptamer or affibody) can be contained in blocking reagent.

Blocking reagent in that respect refers to any substance, of biological or other origin, which can mitigate the unintended or unspecific binding reactions which usually occur between complex biological samples such as blood or serum and a plurality of antigens on a solid phase. Blocking preferably is free of potentially antigenic protein which could otherwise cause even more unspecific binding and reduced signal to noise generation.

For example, bovine serum albumin (BSA) which is frequently used for simple ELISA procedures as a stabilizing or blocking agent is typically unsuitable when detection of human IgE or IgG is involved, as BSA is both a potential food allergen and a frequent inducer of non-relevant IgG in humans which frequently consume dairy or meat products from cow. Any binding sites blocked by BSA could therefore give even more problems with unspecific background than otherwise if the samples contain the respective anti BSA antibodies of the detected subclass. Similar circumstances make it impracticable to use many cheap and easily available blocking reagents which find frequent use in other areas.

Accordingly, if protein blockers are used, they should not be immunogenic to humans, such as human serum albumin which does normally not bind any human antibodies.

Alternative methods of blocking involve detergents, sugars, polyalcohol or other compounds which can destabilize weak binding between interaction partners which are not as strong and specific as antigen-antibody binding complex (typically with affinity constants of $10^{-9}$ M or less).

The incubation steps with sample or detection reagent (e.g. detection antibody) usually take proportionally the longest time of the total procedure, with incubation times ranging from minutes to several hours. Preferably, incubation of sample takes less than two hours, and incubation with detection reagent takes less than 30 minutes. In case where the detection reagent is already bearing a detectable label the signal generation incubation step can be omitted. Otherwise, in particular when using enzymatic signal generation, typical incubation time with signal generation reagent is preferably below 5 minutes.

During the incubation, the present design of the cartridge allows for agitation of the liquid, thereby mixing the sample and increasing the mass transport of affinity binders to the respective antigens. Preferably the agitation follows a movement along the long side of the cartridge which is mild enough not to let the liquid overflow the receptacles border, yet rigid enough to increase reaction kinetic sufficiently as compared to incubation without mixing.

Alternative, assay kinetics can be increased or controlled by temperature or electromagnetic waves intended to mix the fluid more efficiently.

Detection and Measurement

For the creation of a detectable signal there are several possibilities known to those skilled in the art. In the simplest form, the detection reagent which binds to the antigen sites loaded with the specific immune globulin is directly labelled, either with color or an excitable compound such as a fluorescence dye or gold nanoparticles or colored latex nanoparticles or alike. In such case, the detection does not need any additional steps for signal creation, and the signal can be read directly after washing off the unbound detection reagent.

In a preferred embodiment, enzymatic signal generation is employed by using detection reagents which are conjugated to an enzyme, which converts a substrate contained in the signal generation reagent into a detectable signal.

The enzymes conjugated to the detection reagent include but are not limited to alkaline phosphatase (AP), horse radish peroxidase (HRP) or beta-galactosidase (GAL). These enzymes can create a colored precipitate from a substrate (such as NCIB/NBT) or can create photons from a luminophore conversion (e.g. Lumingen APS-5), or can convert a substrate in order to change the extinction coefficient at a certain wavelength, e.g. o-Nitrophenyl-beta-D-galactopyranosidase, respectively.

If necessary, the enzymatic reaction can be stopped immediately by adding a substance which strongly interferes with the conversion of the substrate by the enzyme, a so called stop solution (e.g. destilled water, EDTA, NaOH, HCl, etc).

In some embodiments, the detection reagent is an anti-human IgE antibody directly labelled with a color compound, gold nanoparticles or colored latex nanoparticles or with an excitable compound. In some embodiments, the detection reagent is anti-human IgG antibody directly labelled with a color, gold nanoparticles, colored latex nanoparticles or with an excitable compound. In some embodiments, the detection reagent is an aptamer or affibody specifically recognizing human IgE or IgG antibodies, where the aptamer or affibody is directly labelled with a color, gold nanoparticles, colored latex nanoparticles or an excitable compound. In some embodiments, the detection reagent is an anti-human IgE or IgG antibody conjugated with an enzyme (e.g., AP, HRP or GAL) and the method includes incubating the array with a signal generation reagent (e.g., a substrate for the enzymatic reaction) according to step (iv) of the method described herein, and optionally further adding a stop solution (e.g. ddH2O, EDTA, NaOH, hydrochloric acid, sulfuric acid, or any reagent which can interfere with the enzymatic reaction, either by making the reaction impossible because of pH value requirements for the katalytic reaction, by destroying or altering he substrate chemically, by blocking the active center of the enzyme, or slowing reaction to an insignificant level, etc) following step (iv).

In some embodiments, the detection reagent comprises two components: (i) a first component comprising an anti-IgE or anti-IgG antibody; and (ii) a second component comprising a reagent recognizing the anti-IgE or anti-IgG antibody, which second reagent is either directly labelled with color or excitable compound or conjugated with an enzyme and wherein the antigen array is incubated with the (i) and then (ii) according to step (iii) of the methods described herein (with a washing step in between). For example, the first component may be an anti-IgE or anti-IgG-antibody of a specific type such as an antibody obtained from an organism such as rat, mouse, rabbit, etc., and the second component may be an antibody binding to said type of antibody, e.g. an anti-rat, anti-mouse, anti-rabbit antibody etc.

Specifically provided herein, is an in vitro method for detecting IgE antibodies associated with allergy comprising,
(i) Providing an allergen array as described herein,
(ii) Incubating the array with a sample (e.g. serum or whole or processed blood),
(iii) Incubating the array with an anti-IgE antibody or anti-IgE aptamer directly labeled with a detectable signal or an anti-IgE or anti-IgE aptamer conjugated to an enzyme (e.g. conjugated to AP, HRP or GAL),
(iv) Optionally, incubating the array with a signal generation reagent (e.g., a substrate for the enzymatic reaction),
(v) Optionally adding a stop solution to end signal generation (e.g. ddH2O, EDTA, NaOH, hydrochloric acid, sulfuric acid, or any reagent which can interfere with the enzymatic reaction, and
(vi) Measuring a detectable signal. The detection of a colored signal can proceed via a simple CCD camera, a CMOS camera, a laser scanner such as a conventional flatbed scanner, or any other device capable of measuring the intensity difference between the usually white or transparent background of the solid support and the colored reaction sites where the binding reaction was detected. In case of photon measurement, it is required to use a camera with sufficient sensitivity or a photomultiplier device in order to measure the signals individually.

For the quantification, it is required to first identify the areas where the individual antigens have been immobilized. This can be facilitated by a pattern of positive control spots which always give a detectable and strong signal, so called marker spots. For example, a positive control spot can be a group of beads coupled with a purified human IgE antibody. From the position and the orientation of the marker spots, the relative position of all other sites as well as their size is known and can be located within the acquired image or array of data points.

For each typically round area of immobilized antigen charged particles, a signal integration can be calculated by adding each pixel which lies within the expected signal to the total signal, and each pixel which is outside can be added to the background. Additionally, mean, median and standard deviation can be calculated as well for signals as for background. All calculations will be handled by an image analysis software tool such as are known to the skilled person, for example ImageJ from the NIH.

In the methods described herein local background calculation is preferred, which is done by summarizing all pixels which are within three times the diameter of the spot area but not within any of the antigen sites together.

Additionally, statistical control measures can be used to judge on the quality or the reliability of a signal, such as mean to median variation, signal variation, noise variation, and outlier detections.

A threshold either in terms of total measurable signal—background, or in terms of signal to noise ratio is applied to filter raw measurement data. Preferably only signals which are at least 2 fold higher than the background noise variation are considered as positive signals (e.g., a detectable signal).

Normalization and Calibration of Results

After the acquisition of raw measurement data, there are two steps which are required in order to get from the raw analytic data to clinically relevant response units.

In the methods described herein two distinct methods for achieving first normalization and second calibration of results are employed.

Normalization in that respect is the process of normalizing variations in overall signal levels between measurements, days, lots or operators, to an identical level in average. In such way, variations in the exact timing of incubation, differences because of ambient temperature variations, variations caused by the sample matrix etc. can be compensated to some extent.

For the present application, a standard curve of the specific antibody subclass to be measured in the assay is used to achieve this normalization. A purified antibody, for example human IgE, is immobilized in increasing concentrations at distinct sites of the macroarray format. According to this approach, the highest concentration on the standard curve would be considered a 100% signal, whereas each known dilution of the standard curve gets assigned the corresponding reduction in concentration value. From all points of the curve, a curve fit is calculated and used to transform arbitrary intensity units into relative signal units by applying the curve equation to each raw measurement value.

This method allows for normalizing the average signal intensities between measurements, can however not compensation individual fluctuations for each individual parameter on the respective batch. Typically, there is a certain extent of manufacturing variation in each produced lot, and often these variations are systematic in a way that for example, parameter 1 might be 10% higher than then long time average, and parameter 2 might be 5% lower than the long time average and parameter 3 might be within specifications. In order to eradicate such differences to a necessary minimum, it is feasible to detect any systematic variation from the long time average using well defined control samples already at the manufacturer's quality control site. Once this systematic variation is identified, it is feasible to communicate these differences to the end user in form of a data sheet, or preferably an automatic coding format such as a 2D barcode printed on each batch. By reading and interpreting this barcode, the end user could—facilitated by software tools—automatically adjust the measurement values according to the identified variations during the QC procedure at the manufacturers site, and in the example above then adjust parameter 1 measurements by reducing them by 10%, adjusting parameter 2 by increasing them by 5% and leaving parameter 3 unchanged. Consequently, it shall be possible to reduce the total variation of the immunoassay to a lower level than without this configurable and statistically justified data adjustment.

In a final step, the actual calibration of results has to be achieved. Calibration in this respect is the process of converting adjusted relative response units in some form of absolute units. The absolute units shall serve as a value which allows to compare results to the systems of other manufacturers, between labs or between points in time, even when significant changes to the system have been made.

A calibration can be made against an internationally accepted reference preparation, if such is available. For many disease areas, quantitative reference standards can be purchases and used for calibration. The normal process of calibration is however not practical for use in multi-parameter assay formats, simply because it would require significantly more efforts and costs to calibrate a system than to do the actual measurements.

A standard approach for calibration in single parameter assays is a homologous calibration, whereby a measurement result for a particular antigen—antibody interaction which shall be measured from a sample with unknown concentration of the latter is measured and compared against the measurement results of defined samples with defined concentrations of immunoglobulins against the respective antigen and using this reference curve for transforming raw measurement into absolute quantified measurement results.

This is easily achieved when measuring relatively few standard preparations for calibration purposes as compared to a relatively high number of unknown samples.

In an application however with several hundred individual parameters measured in each reaction, and each parameter representing the binding of the identical antibody subclass but against a different antigen, a homologous calibration curve for each individual parameter is not feasible and would most likely introduce significant additional variation. Therefore, a so called heterologous calibration approach is employed. A calibration curve is not produced for a single antigen-antibody measurement with different concentrations of the respective antibody measured in distinct samples, but with a single sample which presents a range of specific antibody concentrations against a range of different immobilized antigens. The method relies in the fact that when the same immunoglobulin is detected for the binding against different antigens, it is not an absolute requirement to calibrate the antibody response for each target antigen individually but keep the same calibration curve just for each class of immunoglobulin which is detected.

Interpretation of Results Supported by Software Tools

The described application of multi-parameter immunological measurements will produce significantly more test results than a normal single parameter based clinical workup of a patient's sensitization profile.

Consequently, the application of bioinformatics tools shall facilitate the interpretation and visualization of the results into a format which will allow the physician to more easily review the data and get whenever possible the best diagnostic conclusion. The following factors have to be considered relevant for the software facilitated presentation or guidance:

1) General classification of a medical condition, for example, based on the profile, is it likely that the patient suffers from the alleged disease for which the test was ordered.

2) Detailed classification of the disease, for example relevant parameters or patterns of parameters which indicate the status of the disease or the cause of the disease.

3) Risk classification of the patient, for example by distinguishing patients in the level of antibody response against certain targets, or the patterns of antibody responses against a combination of targets, or the absence of protective antibodies against certain targets, or the ratio of different antibody subclasses against different antigen targets.

4) The consequences for the treatment of the patient, for example by choosing appropriate medication, giving the right recommendations for avoidance or even avoiding to administer most likely ineffective medications.

Complete Panels for Clinical Interpretation

The main advantage of a highly multiplexed immunoassay is the possibility to include all relevant clinical parameters into a single test, which reduces the burden on the physician to pre-select tests for each single patient, and always get complete clinical workup in a single analytical step.

Cartridges Design and Advantages in Relation to Automation

Further provided herein are cartridges comprising a test chamber for any of the antigen array described herein, a reservoir for liquid waste and optionally a barcode for identification and calibration. The cartridge may further comprise reservoirs or integrated vials for any one or more of a detection reagent (e.g., labelled antibody, labelled aptamer or labelled affibody), a signal generation reagent (e.g. an enzyme substrate), and a stop solution (e.g. destilled water, EDTA, NaOH, HCl, etc). In some embodiments, the cartridge further comprises a reservoir or integrated vial for one or more control samples (e.g. positive and/or negative controls) and/or one or more buffers used during the assay procedure (e.g. wash buffers, blocking buffers, dilution buffers). In some embodiments, the positive control sample is a commercially available standardized sample with a defined amount of immunoglobulin (e.g. total IgG or IgE and/or defined IgG or IgE specific for a particular antigen/allergen). In some embodiments, a positive control sample is a sample that has been validated or tested positive in a standard assay for the respective immunoglobulin. In some embodiments, the negative control sample is a commercially available sample that does not contain any immunoglobulins or a sample that has been validated or tested negative in a standard assay for the respective immunoglobulin. The cartridge may further provide means for gently moving the antigen array within the test chamber or the test chamber as a whole with the antigen array placed in it to ensure equal distribution of the sample and buffers on the array during incubation periods as well as thorough washing of the array. The dimension of the cartridge will depend on the size of the array and the type and number of reagents used. Preferably the size will be in the range of 1 cm×1 cm×5 cm to 2 cm×5 cm×15 cm.

The fixation of the antigen arrays into the cartridge can be done by one of several ways, including the mechanical fixation by cutting to precise dimension of the surrounding, using mechanical fixations at the edges of the strips, or using biocompatible adhesives which also withstand the washing and incubation steps during the ELISA procedure. The important aspect of the fixation is not to create gaps, areas or holes in the cartridge or between cartridge and solid phase test strip where unspecific binding can occur during the incubation steps, which might not be amenable to efficient washing, as this would greatly increase the overall unspecific signal generation in the detection step and therefore reduce the peak signal to noise of the assay and the overall assay performance.

Of similar importance is the factor of not having position effects of the incubation and signal detection, such as are well known to those skilled in the art. A typical bias is the so called edge effect, which results in reaction sites (spots) close to the border of the array and the adjacent cartridge surrounding walls or vials being either significantly and reproducibly higher or lower than those in the middle of the arrays. The difference can be caused by the behavior of liquid during agitation or mixing, accumulation of binders at selected locations, or by surface tension, or by kinetic differences of the reaction sites surrounded by more fixed borders and therefore more limited free diffusion than those who are more central and less inhibited by edges or walls. Even spatial temperature differences could play a role in the observed differences, as well as a bias in the detection event caused by the geometry of the vessel. An example is that having microarrays deposited in circular micro-well plates, the spots in the center typically behave much different than the spots closer to the boarder of the plates. Though some manufacturers overcome this limitation by printing "circular arrays" or patterns, this or course massively reduces the usable area and number of features per area, which would not be suitable for a real multi-parameter assay with several hundred distinct assays in the reaction.

The cartridge design in the presented invention offers an additional advantage. The cartridge can be almost considered a kit itself, it can contain all liquids and reagents required for the test procedure in therefore designed receptacles. The cartridge may include a barcode for lot identification and even corrective factors for calibration etc. could be stored in such barcode.

Similar, a set of disposable plastic tips can be on board in the cartridge, from where a pipettor could grab them for the process and reinject them into the cartridge after use. In that way it does not incur the surrounding system parts (e.g. the liquid handling) to be in contact with liquids which are potentially biohazard of infectious, as all liquids get collected in the cartridge itself by the designed waste receptacle. Therefore, there is no need for any special cleaning or disinfection procedures for the instrument.

Since the cartridge can both capture or even contain all required liquids for the test procedure, based on such design it is feasible to design the assay automation in a way that the only liquid handling part can be an air displacement pipettor, which using disposable tips does not need to be maintained or any valves or tubing's replaced for the normal expected life time of an instrument. The overall development cost as well as the cost of ownership of such an almost maintenance free instrument are much lower than those for a typical automatic immune analyzer, which contains many movable parts, valves and tubes which need to be replaced repeatedly.

During the washing steps, the cartridge is simply tilted to one side, so that the contained liquid runs into the reservoir within the cartridge where it is captured and finally disposed.

Further provided herein are kits comprising the antigen array or a cartridge as described herein, a detection reagent, control samples (e.g. positive or negative control), buffers used during the assay and instructions for use. The kit may further comprise a signal generation reagent (e.g. a substrate for an enzyme) and optionally a stop solution (e.g. destilled water, EDTA, NaOH, HCl, etc). In some embodiments, the kit comprises an antigen array (e.g. an allergen array), a detection reagent specific for IgE or IgG (e.g. an anti-IgE or anti IgG antibody, an aptamer or affibody specific for IgE or IgG, either directl labeled or conjugated with an enzyme), buffer solutions (e.g. wash buffers blocking buffers, dilution buffers) and optionally a signal generation reagent (e.g. an enzyme substrate). In some embodiments, the kit further comprises a stop solution (e.g. destilled water, EDTA, NaOH, HCl, etc.).

Further provided herein is an apparatus comprising a chamber for one or more cartridges as described herein, a pipettor and a device for signal detection (e.g. CCD camera, CMOS camera, laser scanner).

The invention furthermore comprises the following items:

1. An antigen array comprising groups of antigen-coated beads fixed on a solid carrier, wherein each group comprises
   (i) beads coated with one detection antigen, or
   (ii) beads coated with a set of detection antigens, preferably wherein the solid carrier is a sheet or plate and wherein the detection antigen is an allergen, an infection marker or an autoantigen.

2. The antigen array of item 1, wherein the detection antigen is a biomolecule made of nucleic acids and/or amino acids, preferably a protein, peptide, antibody or DNA molecule, or an organic or non-organic chemical compound.

3. The antigen array of any one of item 1 or 2, wherein the detection antigen is an allergen.

4. The antigen array of any one of items 1 to 3, wherein the detection antigen is an infection marker.

5. The antigen array of any one of items 1 to 4, wherein the detection antigen is an autoantigen.

6. The antigen array of any one of items 1 to 5, wherein the detection antigen is an antigen produced by recombinant DNA technology or an antigen isolated and purified from a biological material.

7. The antigen array of any one of items 1 to 6, wherein the set of detection antigens is obtained from an extract or lysate from a biological source material containing more than one antigen.

8. The antigen array of any one of items 1 to 7, wherein the detection antigen comprises a single epitope, a single macromolecule with several antibody binding epitopes or a mixture of various proteins with different antigens containing a variety of epitopes.

9. The antigen array of any one of items 1 to 8, wherein the beads are micro- or nanobeads.

10. The antigen array of any one of items 1 to 9, wherein the beads have a size between 5 and 500 nm in diameter, preferably between 200 and 500 nm in diameter.

11. The antigen array of any one of items 1 to 10, wherein the beads are latex beads, polymeric plastic beads, preferably polystyrene beads, beads made of biocompatible polymers, or glass beads, preferably silica beads.

12. The antigen array of any one of items 1 to 11, wherein the surface of the beads is porous or non-porous.

13. The antigen array of any one of items 1 to 12, wherein the detection antigen is coupled covalently or non-covalently.

14. The antigen array of any one of items 1 or 13, wherein the detection antigen is coupled to the beads non-covalently by passive adsorption, preferably by hydrophobic and/or electrostatic attachment.

15. The antigen array of any one of items 1 to 14, wherein the detection antigen is coupled via antigen spacers.

16. The antigen array of any one of items 1 to 15 wherein the detection antigen is coupled in a way that creates a preferred orientation for the presentation of epitopes presented on the bound antigen 17. The antigen array of any one of items 1 to 16, wherein the solid carrier is a sheet or plate of a porous or non-porous material, preferably a nitrocellulose sheet, more preferably a laminated nitrocellulose sheet.

18. The antigen array of any one of items 1 to 17 comprising beads of the same or different type.

19. The antigen array of any one of items 1 to 18, wherein the array comprises at least 25 different groups.

20. The antigen array of any one of items 1 to 19, wherein the groups of antigen-coated beads are fixed on the solid carrier using contact methods or non-contact methods, preferably using a solenoid dispensing system.

21. The antigen array of any one of items 1 to 20, wherein each group is fixed as addressable element in a rectangular array or an orange packed array, preferably at densities of 1 addressable element per $mm^2$.

22. The antigen array of any one of items 1 to 3 and 6 to 21 wherein the antigen-coated beads are allergen-coated beads fixed on a solid carrier, preferably the solid carrier is a sheet or a plate, wherein each group comprises
(i) beads coated with one allergen, or
(ii) beads coated with a set of allergens, preferably an allergen extract.

23. Method of detecting an immunoglobulin specific for a detection antigen or for a set of detection antigens comprising
(i) providing an antigen array according to any one of items 1 to 22,
(ii) incubating the array with a sample,
(iii) incubating the array with a detection reagent,
(iv) optionally incubating the array with a signal generation reagent, and
(v) measuring a detectable signal.

24. The method of item 23, wherein the immunoglobulin is an IgE antibody associated with allergy.

25. The method of item 23 wherein the immunoglobulin is an IgG antibody associated with an infection or an autoimmune reaction.

26. The method of any one of items 23 to 25, wherein the sample is a biological fluid, preferably serum, whole or processed blood, nasal fluid or urine, a cell lysate or a tissue homogenate from a subject or a pool of subjects.

27. The method of any one of items 23 to 26, wherein the dectection reagent is an affinity binder specific for the immunoglobulin, preferably an antibody, an aptamer or an affibody.

28. The method of any one of items 23 to 27, wherein the detection reagent is an anti-IgE antibody, an IgE specific aptamer, an IgE specific affibody, anti-IgG antibody, an IgG specific aptamer, or an IgG specific affibody. The method of any one of items 23 to 27, wherein the detection reagent is (i) directly labeled, preferably with a colored or fluorescent compound or with gold nanoparticles or colored latex nanoparticles; or (ii) conjugated to an enzyme.

29. The method of any one of items 23 to 28, further comprising incubating the array with a signal generation reagent according to step (iv) of item 23, wherein the detection reagent is conjugated to an enzyme and the signal generation reagent comprises a substrate for said enzyme.

30. The method of item 30, further comprising the array with a stop solution following step (iv).

31. The method of any one of items 23 to 30 for detecting an IgE antibody associated with allergy comprising,
(i) providing an antigen array according to item 22
(ii) incubating the array with a sample,
(iii) incubating the array with a detection reagent (e.g. an anti-IgE antibody or IgE specific aptamer or IgE-specific affibody)
(iv) optionally incubating the array with a signal generation reagent, and
(v) measuring a detectable signal.

32. A cartridge comprising a test chamber for the antigen array of any one of items 1 to 22, a reservoir for liquid waste, and optionally a barcode.

33. A kit comprising an antigen array according to any one of items 1 to 22, a detection reagent, one or more buffers, one or more control samples and instructions for using the kit in a method according to any one of items 23 to 31, and optionally a signal generation reagent.

34. An apparatus comprising a chamber for one or more cartridges according to item 32, a pipettor and a device for signal detection.

EXAMPLES

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention.

Example 1

Materials and Methods

Allergenic Source Material

Allergens were purchased from various external provides or produced in house. Allergens were either allergenic extracts, purified natural allergens or recombinant allergens. Allergens were treated according to recommendations of suppliers or according to our in-house experience regarding buffers and storage conditions. Repeated freezing/thawing was avoided. For allergens which were delivered in lyophilized form, reconstitution was done according to the manufacturer's instructions.

Allergen Coupling to Nanoparticles

Polystyrene nanoparticles were purchased from Polysciences Europe GmbH.

Coupling of allergen materials to the particles was done following the recommendations provided by the manufacturer, but ultimately had to be optimized for each allergen preparation. A variety of different approaches have been applied in order to get optimal coupling efficiency and biological activity. Some allergens could be coupled by passive adsorption with satisfactory results, while many allergens required special coupling conditions or covalent coupling strategies. For this purpose, polystyrene particles with NH2 or COOH surface modifications were used, as well as homo- or heterobifunctional crosslinkers. Several allergen preparations had to be treated in a way that they were first split up into several aliquots, those then coupled via different conditions and finally pooled again in order to represent the full allergen epitope repertoire during functional testing.

Passive Adsorption Coupling (Standard Protocol)

Nanoparticles were prepared according to instructions from the manufacturers. Allergens or allergen extracts were diluted to the applicable coupling concentration, typically less than 0.5 mg/ml, in buffers matching the isoelectric point of the allergens. Particles (1% solids) and allergens were incubated for 3 hours at room temperature under constant end-to-end mixing. Incubation was continued without mixing over night at 2-8° C. Finally, particles were pelleted by centrifugation at 10.000 rpm, 4° C. for 15 minutes, supernatant was collected and beads suspended in appropriate buffers and preservatives for prolonged storage.

Passive Adsorption Coupling (Advanced Protocol)

Similar to the above standard protocol, but at least 3 different pH ranges were used individually, typically in neutral, acidic and basic range. After the execution of the coupling protocol, particles were pooled back together at neutral pH.

Chemical Coupling by COOH Surface Particles

Nanoparticles were diluted to appropriate concentrations, typically 1% solids, then washed 3× in activation buffer (e.g. MES buffer with pH between 5 and 7.5), pelleted and suspended in between washing steps. For activation, particles containing surface COOH groups were activated with a water soluble carbodiimide, e.g. 1-Ethyl-3-(3-dimethylaminopropyl) carbodiimide for 15-30 minutes. After the activation, particles were washed in activation buffer two more times. Protein was diluted in coupling buffer not containing any free NH2 groups to a concentration which was typically optimized by titration experiments. Activated particles and protein solution was incubated for at least 3 hours at room temperature or overnight at 2-8° C. Finally, particles were pelleted by centrifugation as described above and suspended in storage buffers containing preservatives until further use.

Chemical Coupling by NH2 Surface Particles

A very similar protocol as described above was used, with the distinction that an amino reactive reagent, e.g. glutaraldehye, or succinimide chemistry such as EGS crosslinkers was used to activate the NH2 groups on the nanoparticles. Accordingly, buffers and pH values had to be adjusted to optimize the coupling efficiency for each chemistry applied. Not in all cased did the theoretically optimal pH value give the desired optimal coupling efficiency, but rather a pH value that would not have been chosen by looking at the theoretical properties of a protein.

Assessment of Coupling Efficiency

The coupling efficiency was measured using both direct and indirect methods. Before and after coupling, protein concentration in solution was measured. The degree of protein depletion from the solution after coupling was a good indicator of protein binding but not of biological activity. Additionally, coupled beads were stripped from protein using methods as described by the provider to get protein off the beads. Those stripped-off protein preparations were also characterized using concentration measurement, as well as denaturing SDS gel electrophoresis and staining with coomassie blue.

For the final assessment of the biological activity of the coupled allergens, functional measurement was done using the standard assay and analysis procedure (see below), testing specific positive sera for each allergen preparation. The parameters used for testing were: 15 min blocking, 2 hours serum incubation with 1:5 diluted serum samples, 30 min detection antibody incubation.

Dispensing of Allergen Particles to Solid Phase

Nitrocellulose membranes were purchased from GE Healthcare and Pall Europe. A variety of different membrane types were evaluated, with different properties regarding pore size, flow rates or base material.

Dispensing was done with a Biodot AD1520 instrument using optimized settings for movement, aspiration, dispensing and washing cycles. Each allergen preparation was deposited on the solid phase in a volume of at least 20 nano-liter, with a center to center spacing of 1 mm. The final arrays had a geometry of typically 10 columns and 25 rows.

After dispensing, NC sheets were sealed and stored at 2-8° C. until further processing. Before the assay, NC sheets were cut into appropriate sizes and the small vignettes containing the test array placed into the assay cassettes.

Standard Assay Procedure

A test array containing 250 different features which were initially blocked from unspecific binding in a buffer containing high concentrations of non-allergenic protein while gently rocking the array container cassette was generated.

Washing in between process steps was done using Tris-buffered saline with pH 7.4 and 0.2% Tween-20 as detergent (TBS-T).

After blocking, arrays were incubated with patient serum or plasma, under constant gentle rocking for at least 15 minutes. Serum was discarded and the arrays washed several times with TBS-T under gentle agitation.

Following the washing cycles, arrays were incubated with a diluted anti-human IgE antibody, which was labelled with Alkaline Phosphatase (AP). The antibody was then discarded and remaining unbound antibodies washed off several times with TBS-T.

Finally, arrays were incubated with BCIP/NBT color development substrate (5-bromo-4-chloro-3-indolyl-phosphate/nitro blue tetrazolium) for several minutes until sufficient sensitivity was reached, the reaction then stopped and the remaining substrate washed off.

Arrays were dried before scanning or imaging. Images were taken as 24-bit color images and converted to 16-bit grayscale data.

Analysis

Each circular feature was quantified by calculating the median intensity and subtracting a local background from the feature value. A signal-noise ratio of >2 was considered as a positive signal.

Arrays were normalized by a standard curve of immobilized purified human IgE which was spotted together with allergen preparations. In addition, the normalized values were calibrated by using heterologous calibration against a reference sample with multiple positive test results.

Example 2

Figure 1B:
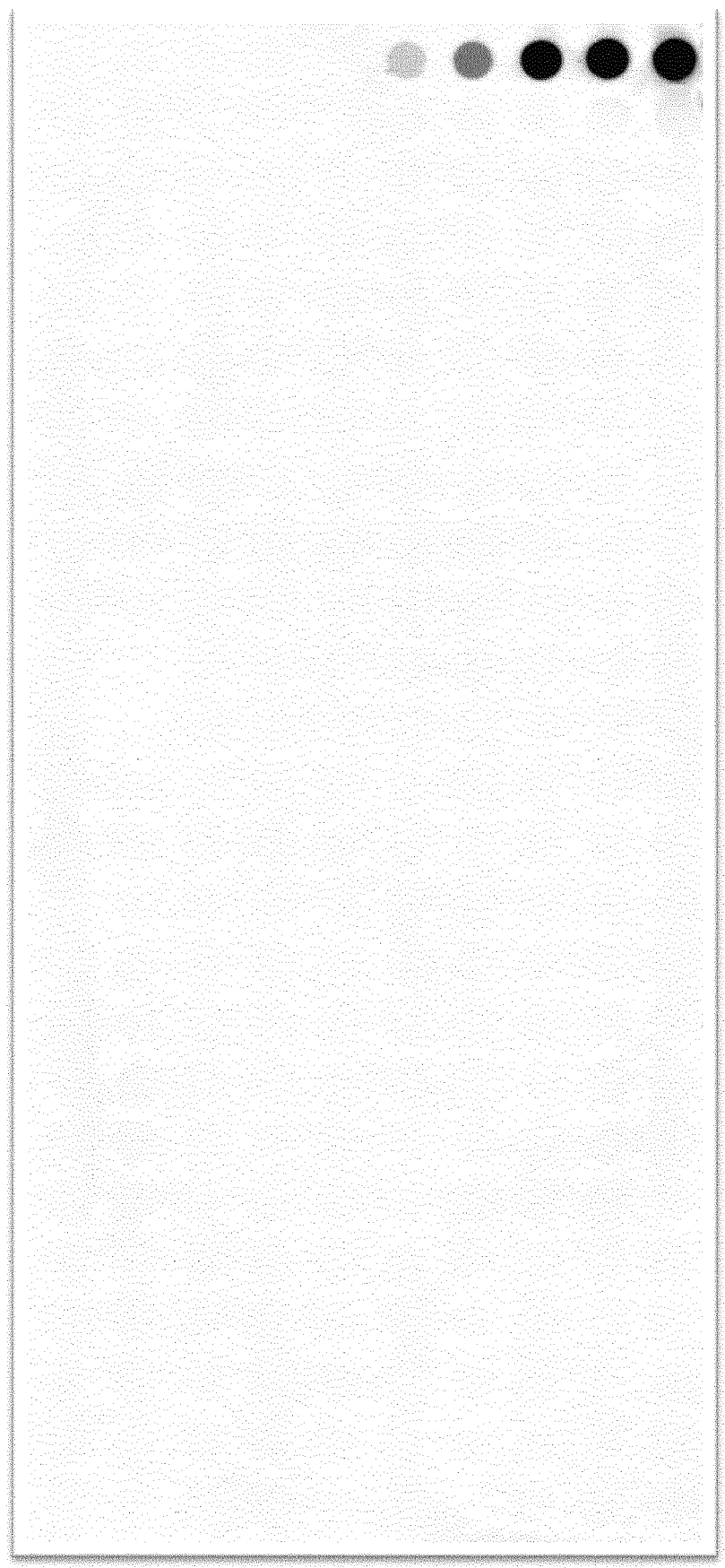

An antigen array comprising 245 groups of antigen-coated beads was generated using the materials and methods described in Example 1. For the data shown here, only passively adsorbed allergens were spotted. Specific IgE measurements for the 245 allergens and 5 IgE standards using a pooled human sample from several allergic subjects are shown in FIG. 1 A. A respective negative sample with no significant level of specific IgE is shown in FIG. 1 B. The layout of the antigen groups is shown in FIG. 1 C. The spacing between antigen groups was 1 mm in x and y direction.

Example 3a

Test Evaluation by Comparing to Reference Method
In total up to 137 patient samples (number of patients listed as n in table 3) were tested with the disclosed method as described in Example 1. Patient samples were diluted 1:5 for the testing, and the standard assay procedure was applied. For the data comparison, the obtained results were compared to the available reference data which were produced using different version of the ImmunoCAP ISAC test (Thermo Fisher, Uppsala, Sweden). Patient samples tested positive or negative in the reference assay are shown in Table 3 as "pos" or "neg", respectively. For the data comparison, Medcal Version 16.1 was used to create ROC statistics (Response Operator Curve). For this purpose, any antigen specific results higher than the manufacturers cutoff in the ImmunoCAP ISAC test was considered as true positive (=1), otherwise as true negative (=0). The output of the statistic evaluation was: Area under the curve AUC (perfect correlation=1, no correlation=0), analytic sensitivity, analytic specificity. In total, 3619 measurement results, whereof 692 positive results and 2927 negative results were taken into account. Results are summarized in table 3 below. The average sensitivity and specificity are also shown, which were 99% and 95% respectively, whereby the reduced specificity can be explained by the higher sensitivity of the new method which will generate more positive measumrent results than the reference.

TABLE 3

ROC analysis with reference data from ImmunoCAP ISAC

| Parameter | Reference test | n | pos | neg | AUC | Sens | Spec |
|---|---|---|---|---|---|---|---|
| Alt a 1 | Alt a 1 | 137 | 9 | 128 | 0.99 | 100 | 95 |
| Ani s 3 | Ani s 3 | 81 | 4 | 77 | 1.00 | 100 | 100 |
| Art v | Art v 1 | 81 | 4 | 77 | 0.96 | 100 | 94 |
| Art v 1 | Art v 1 | 137 | 8 | 129 | 1.00 | 100 | 99 |
| Bet v 1.0101 | Bet v 1 | 81 | 10 | 71 | 0.93 | 100 | 79 |
| Bet v 2.0101 | Bet v 2 | 81 | 10 | 71 | 0.99 | 100 | 99 |
| Bos d 4 | Bos d 4 | 81 | 4 | 77 | 1.00 | 100 | 100 |
| Bos d 5 | Bos d 5 (2x) | 81 | 4 | 77 | 0.99 | 100 | 99 |
| Bos d 8 | Bos d 8 | 81 | 5 | 76 | 1.00 | 100 | 99 |
| Bos d LF | Bos d LF | 81 | 2 | 79 | 0.90 | 100 | 84 |
| Can f 1 | Can f 1 | 81 | 6 | 75 | 1.00 | 100 | 99 |
| Can f 3 | Can f 3 | 81 | 3 | 78 | 1.00 | 100 | 100 |
| Cup a 1 | Cup a 1 | 56 | 26 | 30 | 0.98 | 100 | 97 |
| Der p 1 | Der p 1 | 137 | 47 | 90 | 0.99 | 97 | 98 |
| Der p 10 | Der p 10 | 81 | 3 | 78 | 1.00 | 100 | 100 |
| Fel d 1 | Fel d 1 | 81 | 29 | 52 | 0.98 | 97 | 94 |
| Gal d 1 | Gal d 1 | 81 | 4 | 77 | 1.00 | 100 | 100 |
| Gal d Egg White | Gal d 1, 2, 3, 4 | 81 | 6 | 75 | 0.92 | 100 | 77 |
| Hel as | Hel as 1 | 81 | 3 | 78 | 0.75 | 100 | 63 |
| Hel as 1 | Hel as 1 | 81 | 3 | 78 | 1.00 | 100 | 99 |
| Hev b 6.02 | Hev b 6 | 81 | 5 | 76 | 1.00 | 100 | 100 |
| Hev b 8 | Hev b 8 | 81 | 12 | 69 | 0.95 | 92 | 96 |
| Lol p 1 | Lol p 1 | 137 | 74 | 63 | 0.99 | 98 | 93 |
| Mer a 1 | Mer a 1 | 81 | 13 | 68 | 0.98 | 92 | 93 |
| Ole e 1 | Ole e 1 | 137 | 42 | 95 | 0.98 | 96 | 94 |
| Ole e 2 | Ole e 2 | 137 | 25 | 112 | 1.00 | 100 | 100 |
| Par j 2 | Par j 2 | 137 | 44 | 93 | 0.99 | 97 | 94 |
| Pen m 1 | Pen m 1 | 81 | 4 | 77 | 1.00 | 100 | 100 |
| Per a 7 | Per a 7 | 81 | 4 | 77 | 0.98 | 100 | 92 |
| Phl p 1 | Phl p 1 | 137 | 87 | 50 | 1.00 | 100 | 100 |
| Phl p 2 | Phl p 2 | 137 | 44 | 93 | 0.95 | 100 | 91 |
| Phl p 5 | Phl p 5 | 137 | 61 | 76 | 1.00 | 100 | 100 |
| Phl p 6 | Phl p 6 | 137 | 40 | 97 | 0.99 | 100 | 98 |
| Phl p 7 | Phl p 7 | 81 | 3 | 78 | 1.00 | 100 | 100 |
| Phl p Pollen | Phl p 1, 2, 5, 6, 7 | 56 | 31 | 25 | 0.98 | 97 | 92 |
| Pla a 1 | Pla a 1 | 81 | 2 | 79 | 1.00 | 100 | 100 |
| Pla a Pollen | Pla a 1, 2 | 81 | 6 | 75 | 0.94 | 100 | 91 |
| Pru p 3 | Pru p 3 | 56 | 5 | 51 | 0.98 | 100 | 90 |
|  |  | Sum | Sum | Sum | — | Average | Average |
| STATISTICS |  | 3619 | 692 | 2927 |  | 99 | 95 |

Example 3b

Test Evaluation by Comparing to Reference Method 220 patient samples were tested with the disclosed method as described in Example 1. Allergens were either passively adsorbed or chemically coupled, e.g. using different chemical linkers. Patient samples were diluted 1:5 for the testing, and the standard assay procedure was applied. For the data comparison, the obtained results for were compared to the available reference data which were produced using different version of the ImmunoCAP ISAC test (Thermo Fisher, Uppsala, Sweden). Sensitivity, specificity and r2 correlation for selected allergens are shown in FIG. 2. Sensitivity and specificity were evaluated using MedCalc, against reference data using the manufacturers protocols for testing and cut-off 0.3 ISU. Linear regression analysis of measurement results was performed with Microsoft Excel. In total, 779 positive results and 2772 negative results were taken into account.

Example 4

Signal Amplification 12 allergen extracts or molecular allergens from milk and egg were immobilized under two different conditions to the solid phase carrier material (nitrocellulose Protran, 0.2 um, GE Healthcare). The first condition was directly coupling the allergenic proteins to the solid phase as described by the manufacturer for western blotting procedures. Secondly, the 12 allergens were first coupled to 350 nm sized polystyrole nanoparticles by passive adsorption under neutral pH conditions without further optimization of the coupling conditions as described in materials and methods of Example 1.

Then, 20 milk and egg allergic patient sera were tested for specific IgE against the 12 proteins. The obtained allergen specific signals from each directly immobilized protein preparation or each immobilized particle-coupled antigen (raw data for all 20 sera shown in Table 5) were averaged over all 20 sera, the two summary values per allergen were compared, and a factor was calculated between these values. The results are presented in Table 4 and FIG. 3.

TABLE 4

Summary results for 12 allergens either directly immobilized or immobilized as particle coupled preparations. Raw intensity measurement data is shown, uncalibrated. The average signal amplification was almost 8-fold when allergens were coupled to particles as compared to allergens not coupled to particles, ranging from a factor of almost 2-17. The results are represented graphically in FIG. 3.

| Allergen | Direct | Particle coupled | Factor (x) |
|---|---|---|---|
| Bos d [Milk] | 226308 | 685342 | 3.03 |
| Bos d 4 | 29706 | 98222 | 3.31 |
| Bos d 5 | 50009 | 278392 | 5.57 |
| Bos d 6 | 7291 | 127222 | 17.45 |
| Bos d 8 | 151474 | 606300 | 4.00 |
| Bos d LF | 80338 | 342786 | 4.27 |
| Gal d [Egg White] | 40472 | 77736 | 1.92 |
| Gal d [Egg Yolk] | 29165 | 75288 | 2.58 |
| Gal d 1 | 14947 | 179650 | 12.02 |
| Gal d 2 | 2702 | 28958 | 10.72 |
| Gal d 3 | 5169 | 82668 | 15.99 |
| Gal d 4 | 5533 | 61884 | 11.18 |

TABLE 5

Detailed raw measurement data from signal amplification example

| | Serum 1 | Serum 2 | Serum 3 | Serum 4 | Serum 5 | Serum 6 | Serum 7 | Serum 8 | Serum 9 | Serum 10 |
|---|---|---|---|---|---|---|---|---|---|---|
| *Directly immobilized* | | | | | | | | | | |
| Bos d [Milk] | 0 | 3906 | 5274 | 8670 | 6891 | 13878 | 36391 | 1062 | 1219 | 2141 |
| Bos d 4 | 0 | 439 | 251 | 760 | 856 | 868 | 10352 | 0 | 220 | 396 |
| Bos d 5 | 0 | 903 | 211 | 224 | 0 | 0 | 7903 | 0 | 522 | 788 |
| Bos d 6 | 0 | 0 | 0 | 0 | 0 | 0 | 1205 | 0 | 758 | 0 |
| Bos d 8 | 0 | 2824 | 2836 | 5907 | 931 | 1098 | 32502 | 610 | 1054 | 1813 |
| Bos d LF | 0 | 1417 | 766 | 213 | 233 | 215 | 2340 | 0 | 0 | 2467 |
| Gal d [Egg White] | 0 | 0 | 2369 | 0 | 0 | 0 | 1434 | 0 | 0 | 690 |
| Gal d [Egg Yolk] | 0 | 1142 | 7272 | 947 | 0 | 0 | 0 | 0 | 0 | 0 |
| Gal d 1 | 0 | 772 | 384 | 385 | 133 | 0 | 3502 | 0 | 574 | 0 |
| Gal d 2 | 0 | 0 | 0 | 0 | 0 | 0 | 2702 | 0 | 0 | 0 |
| Gal d 3 | 0 | 0 | 0 | 0 | 0 | 0 | 1572 | 0 | 0 | 0 |
| Gal d 4 | 0 | 251 | 0 | 184 | 0 | 0 | 1053 | 163 | 0 | 0 |
| *Particle coupled protein* | | | | | | | | | | |
| Bos d [Milk] | 0 | 24132 | 22258 | 15548 | 9922 | 16500 | 78268 | 7626 | 10772 | 20808 |
| Bos d 4 | 0 | 1896 | 936 | 522 | 0 | 0 | 5976 | 0 | 428 | 2178 |
| Bos d 5 | 0 | 6174 | 3316 | 2018 | 1046 | 1030 | 37328 | 3970 | 5512 | 6592 |
| Bos d 6 | 0 | 4846 | 2054 | 3386 | 1916 | 2192 | 5196 | 2038 | 13192 | 4702 |
| Bos d 8 | 366 | 28778 | 18830 | 12498 | 4772 | 1844 | 74110 | 9668 | 6742 | 13908 |
| Bos d LF | 0 | 32520 | 4386 | 11362 | 7206 | 7902 | 8260 | 2330 | 1504 | 15356 |
| Gal d [Egg White] | 0 | 0 | 17398 | 0 | 0 | 0 | 4956 | 0 | 530 | 0 |
| Gal d [Egg Yolk] | 0 | 2696 | 18090 | 1914 | 384 | 0 | 0 | 1128 | 0 | 0 |
| Gal d 1 | 0 | 27028 | 6558 | 6118 | 2630 | 406 | 13438 | 6482 | 4488 | 476 |
| Gal d 2 | 0 | 1538 | 252 | 394 | 0 | 418 | 7826 | 2264 | 400 | 810 |
| Gal d 3 | 0 | 12624 | 2868 | 3170 | 558 | 0 | 4392 | 2072 | 0 | 0 |
| Gal d 4 | 0 | 10240 | 1414 | 3690 | 1248 | 0 | 3244 | 2212 | 0 | 0 |

TABLE 5-continued

Detailed raw measurement data from signal amplification example

|  | Serum 11 | Serum 12 | Serum 13 | Serum 14 | Serum 15 | Serum 16 | Serum 17 | Serum 18 | Serum 19 | Serum 20 |
|---|---|---|---|---|---|---|---|---|---|---|
| Directly immobilized | | | | | | | | | | |
| Bos d [Milk] | 3231 | 0 | 38058 | 39992 | 1211 | 1728 | 2446 | 5507 | 49671 | 5032 |
| Bos d 4 | 0 | 0 | 3430 | 672 | 0 | 0 | 0 | 925 | 10537 | 0 |
| Bos d 5 | 727 | 0 | 0 | 421 | 0 | 0 | 0 | 3941 | 33137 | 1232 |
| Bos d 6 | 0 | 0 | 622 | 0 | 4706 | 0 | 0 | 0 | 0 | 0 |
| Bos d 8 | 1124 | 0 | 2842 | 41253 | 0 | 0 | 167 | 4797 | 46058 | 5658 |
| Bos d LF | 10893 | 0 | 224 | 0 | 153 | 0 | 194 | 6197 | 46932 | 8094 |
| Gal d [Egg White] | 1455 | 0 | 0 | 566 | 6034 | 3040 | 0 | 580 | 21523 | 2781 |
| Gal d [Egg Yolk] | 194 | 123 | 0 | 0 | 15901 | 0 | 421 | 0 | 3165 | 0 |
| Gal d 1 | 1916 | 0 | 2690 | 0 | 0 | 1081 | 564 | 0 | 2946 | 0 |
| Gal d 2 | 0 | 0 | 0 | 0 | 0 | 0 | 0 | 0 | 0 | 0 |
| Gal d 3 | 873 | 0 | 2724 | 0 | 0 | 0 | 0 | 0 | 0 | 0 |
| Gal d 4 | 876 | 0 | 1728 | 0 | 0 | 261 | 0 | 0 | 1017 | 0 |
| Particle coupled protein | | | | | | | | | | |
| Bos d [Milk] | 11538 | 4458 | 42316 | 132424 | 8942 | 4634 | 4816 | 28064 | 172130 | 70186 |
| Bos d 4 | 0 | 0 | 0 | 2618 | 0 | 0 | 0 | 3458 | 79354 | 856 |
| Bos d 5 | 4868 | 1454 | 1346 | 6250 | 3056 | 1132 | 1246 | 32904 | 146902 | 12248 |
| Bos d 6 | 2234 | 1332 | 5950 | 476 | 48884 | 5156 | 2518 | 3342 | 16388 | 1420 |
| Bos d 8 | 9590 | 3548 | 5746 | 137612 | 7302 | 2234 | 3398 | 29196 | 173092 | 63066 |
| Bos d LF | 23502 | 1740 | 2554 | 3092 | 1738 | 6904 | 5704 | 11668 | 152712 | 42346 |
| Gal d [Egg White] | 0 | 0 | 0 | 0 | 43004 | 11558 | 0 | 290 | 0 | 0 |
| Gal d [Egg Yolk] | 1110 | 0 | 1026 | 0 | 41200 | 1080 | 1750 | 1748 | 3162 | 0 |
| Gal d 1 | 22762 | 2492 | 48790 | 1700 | 7604 | 6796 | 5254 | 5522 | 11106 | 0 |
| Gal d 2 | 1890 | 0 | 2942 | 0 | 558 | 750 | 1100 | 1382 | 6434 | 0 |
| Gal d 3 | 16954 | 0 | 35786 | 0 | 3890 | 0 | 0 | 354 | 0 | 0 |
| Gal d 4 | 8720 | 0 | 28012 | 0 | 2148 | 514 | 0 | 442 | 0 | 0 |

Example 5

Effect of Different Coupling Conditions on Specific IgE Response in a Functional Assay Specific IgE measurements with 8 different samples positive against Pru p 3, a major allergen from peach were performed (FIG. 4). One negative sample was tested as control. Pru p 3 was coupled using several different methods, including three different covalent coupling methods (condition 1-3). The passive protein adsorption did not work at all and almost no protein could be bound to the nanoparticles just by passive adsorption (results not shown). According to the analysis of the coupling efficiency, not much difference could be observed between the different covalent coupling approaches. However, the functional assay revealed a major difference in the biological activity of the coupled allergens when testing a range of sera and comparing the results to a reference method ImmunoCAP 100 from Thermofisher, Uppsala, Sweden).

Depending on the serum tested, significant differences could be observed between the results from the various methods and coupling approaches. The underlying explanation is that depending on which epitopes the serum has specific IgE against, a certain coupling method or assay method presents more or less of the respective epitope in active conformation.

The values are not directly comparable as each method produces results in different units, which are however internally calibrated to be similar.

Example 6

Case Study of Patient Revealing Additional Sensitizations

A patient visited a local allergy clinic after two asthma attacks during the night when staying overnight at a friend's house with a cat. Grass and Birch allergy was known before but no breathing problems had occoured previously. The results obtained in the allergy clinic using the Immuno CAP method are shown in Table 6 below (Reference IC) and compared to the method described herein (referred to as "FABER" in Table 6). Table 6 further indicates the results of skin prick tests (SPT) and observed symptoms in the patient for selected allergens.

The qualitative correlation (positive or negative) of in vitro results between the method described herein and the reference method ImmunoCAP are generally high. It can be assumed that some of the commercially obtained allergenic extracts (e.g. Bet v, Amb a) are not containing sufficient amount of allergens, as the values obtained were initially lower than the reference method. However, when summarizing the molecular testing results a very similar result could be obtained between our method (Bet v 1.0101+Bet v 2.0101) and ImmunoCAP.

Skin prick test (SPT) in the patient was negative for cat. The skin test as well as the IVD test on the ImmunoCAP system was performed with cat allergen extracts. Both tests performed poorly, giving a negative test in SPT and a moderate positive in the ImmunoCAP test. A general problem with allergenic extracts is that the exact nature of allergens present in the mix is unclear, as well as the degradation of allergens that can happen during extraction or storage. Our test format showed a comparably low result on the commercially obtained cat extract, but a very high positive result on the recombinant pure cat allergen Fel d 1. It is very unlikely that such a high positive in vitro result would have been as easily dismussed from the clinician based on the negative SPT test result.

Additional sensitizations have been found some of which cannot be explained by allergen cross-reactivity, and therefore could be considered as potentially relevant, for example against Shrimp and Cockroach. For example, highly related PR10 type of allergens (Bet v 1 homology) found positive included: Bet v 1.0101, Mal d 1.0108, Cor a 1.0103; Profilins which are also highly conserved between species found positive were: Ara h 8.0101, Bet v 2.0101, Hev b 8, Mer a 1; Also many animal epithelia or animal derived milk or meat proteins can be explained by cross-reactivity between animal species.

On the other hand, the allergens such as Bla g 1 from cockroach or Pen m 1 from shrimp were not found by any reference testing and could be considered as genuine sensitizations that cannot be explained by cross-reactivity to other positive test results. Thus, these proteins could have been investigated further on clinical relevance.

TABLE 6

"Patient A" refers to the FABER diagnostic system

| Allergen | Name | PATIENT A | Reference IC | SPT | Symptoms |
|---|---|---|---|---|---|
| Alt a 1 | *Alternaria* | 6.66 | 1.97 | pos | ? |
| Amb a [Pollen] | *Ambrosia* | 0 | 3.58 | neg | |
| Ana c 2 | CCD Marker | 1.32 | | | |
| Ara h 8.0101 | Profilin, Peanut | 2.9 | | | |
| Arm r HRP | CCD Marker | 1.08 | | | |
| Art v [Pollen] | *Artemisia* | 0 | 4.03 | neg | |
| Bet v [Pollen] | Birch | 1.04 | 60 | pos | pos |
| Bet v 1.0101 | Birch | 17.09 | | | |
| Bet v 2.0101 | Birch | 18.85 | | | |
| Bla g 1 | Cockroach | 1.24 | | | ? |
| Bos d [Milk] | Milk, Cow | 1.64 | | | |
| Can f [Epithelium] | Dog | 3.37 | 0.38 | neg | ? |
| Cor a 1.0103 | Hazel | 10.06 | NA | + | ? |
| Cri c | Rabbit | 2.96 | | neg | |
| Cry j | Cedar | 1.39 | | | |
| Der f 2 | Mites | 1.08 | 0.02 | neg | ? |
| Equ as [Milk] | Milk, Donkey | 3.23 | | | |
| Fel d | Cat | 1.89 | 3.34 | neg | pos |
| Fel d 1 | Cat | 40.88 | | | |
| Hev b 8 | Profilin, Latex | 7.05 | | | |
| Lol p [Pollen] | Grass | 62.06 | | | |
| Lol p 1 | Grass | 46.21 | | | |
| Mal d 1.0108 | Apple | 7.32 | | | |
| Mer a 1 | Profilin, sunflower | 9.52 | | | |
| Mus m [Epithelium] | Mouse | 3.11 | | | |
| Ole e 2 | Olive | 5.3 | | | |
| Ory c [Epithelium] | Hamster | 3.94 | | | |
| Ovi a [Meat] | Meat, Sheep | 2.34 | | | |
| Ovi a [Milk] | Milk, Sheep | 1.07 | | | |
| Ovi a 6 | Grass | 1.4 | | | |
| Phl p | Grass | 51.77 | 76.1 | pos | pos |
| Phl p 1.0102 | Grass | 50.38 | | | |
| Phl p 5.0101 | Grass | 53.09 | | | |
| Phl p 6.0101 | Grass | 10.16 | | | |
| Pla a | Platane | 1.81 | | | |
| Rat n [Epithelium] | Rat | 4.15 | | | |
| Pen m 1 | Shrimp | 0.38 | | | |

Example 7

Test Comparison with Reference Method 83 samples were tested using the antigen array described herein (see Examples 1 and 2) as well as using the ImmunoCAP ISAC test (Thermo Fisher Uppsala, Sweden) as reference method. The technical specifications of the two tests are compared in FIG. 5.

A total of 245 allergens were tested in the antigen array described in Examples 1 and 2, and 112 allergens were tested in the reference method, 70 allergens overlapped between the two tests. The results for these allergens that were directly comparable (identical) between the two tests correlated well, showing a correlation of 76% Pearson. 1057 positive results were obtained for these overlapping allergens in the reference method, while 1159 positive results were obtained with the method described herein, corresponding to an increase of about 10% (9.65%) and indicating increased sensitivity of the present method.

Furthermore, 2508 positive test results were obtained in total with the reference method while a total of 4740 positive results was obtained with the instant method. Thus, the antigen array described herein identified many more sensitizations, i.e., an increase of 89%, further indicating a higher sensitivity of the instant antigen array/method compared to the reference array/method. The results are summarized in Table 7.

TABLE 7

Summary of test comparison

| Summary reference method comparison | |
|---|---|
| # of tested samples | 83 |
| Reference Method | ImmunoCAP ISAC 112 sIgE |
| # reference allergens | 112 |
| # tested allergens | 245 |
| # overlapping (identical) allergens | 70 |
| # directly comparable results | 5810 |
| # positive test results obtained with reference method | 2508 |
| # positive test results obtained with new method | 4740 |
| # positve results reference, overlapping allergens | 1057 |
| # positve results new method overlapping allergens | 1159 |
| % additional sensitizations detected with new method | 89.00% |
| % additional sensitizations detected with new method, overlapping allergens | 9.65% |
| Mean Pearsson Correlation new vs. Reference method | 0.76 |
| Max Pearsson Correlation new vs. Reference method | 0.99 |

Example 8

Stability of Antigen-Coupled Beads

Allergen-coupled beads were prepared as described in Example 1 and an allergen array produced on day 0. Several further antigen arrays (about 40) were produced over a period of 330 days using the same preparations of allergen coupled beads. The antigen-coupled beads were stored during this period at 2-8° C. except for when used for producing an allergen array for which they were kept at room temperature for about 30 min.

The same sample was tested on day 0 in an allergen array produced on day 0 and then again on day 330 in an allergen array produced on day 330. The results of the two tests and the coefficient of variation (CV) are shown in Table 8. FIG. 5 shows a plot of the results on day 0 and day 330.

These data show an extremely high stability of the allergen-coated beads and reproducibility of the method.

TABLE 8

Comparison of test results on day 0 and day 330

| Allergen | Day 0 | Day 330 | CV (%) |
|---|---|---|---|
| *Act d* [Fruit] | 1.97 | 2.34 | 8.51 |
| *All p* | 5.05 | 5.54 | 4.63 |
| *All s* | 4.54 | 5.21 | 6.84 |
| *Alt a* 1 | 11.53 | 12.36 | 3.49 |
| *Ana p* [Egg Yolk] | 1.32 | 1.32 | 0.34 |
| *Ara h* | 2.94 | 3.28 | 5.37 |
| *Ara h* 1-NT | 1.77 | 1.94 | 4.69 |
| *Ara h* 8.0101 | 1.20 | 1.43 | 8.62 |
| *Art v* | 2.21 | 2.60 | 8.12 |
| *Blo t* | 1.44 | 1.61 | 5.47 |
| *Bos d* [Milk] | 10.61 | 11.14 | 2.45 |
| *Bos d* 8 | 9.60 | 10.01 | 2.08 |

TABLE 8-continued

Comparison of test results on day 0 and day 330

| Allergen | Day 0 | Day 330 | CV (%) |
|---|---|---|---|
| *Bub b* [Milk] | 9.55 | 10.31 | 3.83 |
| *Cam d* [Milk] | 2.28 | 2.47 | 4.12 |
| *Can f* [Epithelium] | 11.78 | 12.00 | 0.93 |
| *Can f* 3 | 27.57 | 32.16 | 7.69 |
| *Cap h* [Milk] | 7.16 | 6.58 | 4.18 |
| *Cot c* [Egg white] | 1.18 | 1.35 | 6.87 |
| *Cot c* [Egg yolk] | 2.11 | 2.57 | 9.76 |
| *Cri c* | 2.67 | 2.91 | 4.28 |
| *Der f* 2 | 1.89 | 2.21 | 7.92 |
| *Der p* 10 | 2.31 | 2.49 | 3.84 |
| *Der p* 23.0101 | 2.29 | 2.30 | 0.18 |
| *Equ c* 3 | 1.42 | 1.66 | 7.82 |
| *Fag e* | 1.50 | 1.66 | 4.88 |
| *Fel d* | 1.97 | 1.80 | 4.66 |
| *Fel d* 2 | 12.50 | 13.53 | 3.96 |
| *Gal d* [Egg Yolk] | 1.34 | 1.22 | 4.82 |
| *Gal d* 5 | 2.05 | 1.91 | 3.46 |
| *Hel as* 1 | 1.27 | 1.49 | 8.18 |
| *Jug r* [Seed] | 2.13 | 2.12 | 0.27 |
| *Lup a* [Seed] | 1.24 | 1.28 | 1.49 |
| *Mal d* 1.0108 | 2.54 | 2.98 | 7.95 |
| *Mel g* [Egg yolk] | 1.43 | 1.35 | 2.81 |
| *Ory c* [Epithelium] | 1.94 | 1.68 | 6.99 |
| *Ory c* 6 | 2.76 | 2.75 | 0.23 |
| *Ovi a* [Milk] | 10.90 | 9.59 | 6.38 |
| *Par j* | 5.78 | 6.18 | 3.33 |
| *Phl p* 1.0102 | 5.06 | 6.23 | 10.38 |
| *Phl p* 7.0101 | 3.46 | 3.29 | 2.49 |
| *Pis v* [Seed] | 3.81 | 4.00 | 2.51 |
| *Pla a* | 9.46 | 10.72 | 6.24 |
| *Pru ar* [Fruit] | 5.62 | 5.29 | 3.08 |
| *Pru du* [Seed] | 2.05 | 1.77 | 7.30 |
| *Pru p* [Pulp] | 4.82 | 5.25 | 4.33 |
| *Que a* [Pollen] | 4.59 | 4.41 | 2.00 |
| *Sol so* | 2.26 | 1.92 | 8.14 |
| *Sola l* [Fruit] | 2.86 | 2.95 | 1.43 |
| *Sola l* [Seed] | 3.01 | 3.03 | 0.34 |
| *Sola m* | 2.55 | 2.91 | 6.46 |
| *Tri a* [Seed] | 4.45 | 3.95 | 5.92 |
| *Ven ga* | 2.50 | 2.22 | 5.77 |
| *Zea m* [Seed] | 1.33 | 1.57 | 8.22 |

Example 9

Extract Optimization for Preparing Allergen-Coated Beads

Birch pollen was purchased form a commercial provider and an allergen extract was prepared by methods known to those skilled in the art, basically stirring under defined conditions and timings in a physiological buffer. Birch pollen extract was coupled to nanoparticle by passive coupling using 4 different pH and salt conditions. As the data show (Table 9), based on the molecular profile of the patient (e.g. which molecular allergens the patient has specific antibodies in the serum), different pH values give different quantification of sIgE. This indicates that combining different pH condition preserves the molecular epitope repertoire of the extract and results in a more accurate and more sensitive measurement.

In addition, birch extract was further processed by size exclusion chromatography (SEC). Individual fractions representing a defined molecular weight range of the original extract were collected and coupled to nanoparticles using a single condition. As expected, depending on the molecular recognition pattern, an even more distinguished measurement result is obtained according to the patients' molecular sensitization pattern. For example, sample 1 showed comparable levels of specific IgE in all fractions, while sample 2 showed low levels of sIgE against fraction 1 but high against fraction 3, whereas sample 3 had the highest sIgE levels against fraction 1. Combining the individual fractions and further optimizing the pH coupling conditions for each fraction will results in higher analytical sensitivity than the reference method.

TABLE 9

| Units: specific IgE, in kUA/L (= 2.4 ng/ml) | Sample 1 | Sample 2 | Sample 3 | Sample 4 | Sample 5 | Sample 6 | Sample 7 |
|---|---|---|---|---|---|---|---|
| Birch extrakt, pH Condition 1 | 24.15 | 29.06 | 9.22 | 0 | 0 | 0 | 0 |
| Birch extrakt, pH Condition 2 | 21.3 | 22.28 | 9.51 | 0 | 0 | 0 | 0 |
| Birch extrakt, pH Condition 3 | 26.25 | 28.68 | 18.79 | 0 | 0 | 0 | 0 |
| Birch extrakt, pH Condition 4 | 20.24 | 22.95 | 10.46 | 0 | 0 | 0 | 0 |
| Birch extrakt, Mix of pH conditions 1-4 | 35.18 | 36.22 | 28.75 | 0 | 0.2 | 0 | 0 |
| Birch extrakt, fraction 1 (SEC) | 39.21 | 1.1 | 37.41 | 0 | 0.29 | 0 | 0 |
| Birch extrakt, fraction 2 (SEC) | 26.57 | 8 | 24.79 | 0 | 0 | 0 | 0 |
| Birch extract, fraction 3 (SEC) | 35.29 | 40.15 | 13.25 | 0 | 0.39 | 0 | 0 |
| Sum of SEC fractions 1-3 | 74.5 | 41.25 | 50.66 | 0 | 0.68 | 0 | 0 |
| Reference method (ImmunoCAP) | 29.6 | 77 | 6.04 | 0 | 0.34 | 0 | 0 |
| Molecular Allergen Bet v 1 | + | + | + | − | + | − | − |
| Molecular Allergen Bet v 2 | + | + | + | − | + | − | − |
| Molecular Allergen Bet v 4 | − | − | + | − | − | − | − |

The invention claimed is:

1. An antigen array for detecting allergen-specific Immunoglobulin E (IgE) associated with allergy in a sample comprising allergen-coated polystyrene beads fixed on a solid carrier, wherein the polystyrene beads have $NH_2$ or COOH surface modifications, and wherein the antigen array comprise:
   (i) at least a first sub-population of the polystyrene beads and a second sub-population of the polystyrene beads, wherein each sub-population of the beads has a different characteristic, and wherein each subpopulation of the beads is coated with a same predetermined allergen, or
   (ii) at least a first sub-population of the polystyrene beads and a second sub-population of the polystyrene beads, wherein each sub-population of the beads has a different characteristic, and wherein each subpopulation of the beads is coated with a same predetermined set of different allergens,
   wherein the solid carrier is a sheet or a plate, and wherein the characteristics of the beads are selected from the group consisting of size, material, surface coating, hydrophobicity, electric charge, surface porosity, and allergen coupling chemistry,
   thereby creating an array which presents for binding a variety of epitopes of the same predetermined allergen or the same predetermined set of different allergens and which increases sensitivity of the assay.

2. The antigen array of claim 1, wherein the allergen is a biomolecule made of nucleic acids and/or amino acids, preferably a protein, peptide, antibody or DNA molecule, or an organic or non-organic chemical compound.

3. The antigen array of claim 1, wherein the allergen is produced by recombinant DNA technology or is isolated and purified from a biological material.

4. The antigen array of claim 1, wherein the set of different allergens is obtained from an extract or lysate from a biological source material containing more than one allergen.

5. The antigen array of claim 1, wherein the beads are micro- or nanobeads, preferably wherein the beads have a size between 5 and 500 nm in diameter, preferably between 200 and 500 nm in diameter.

6. The antigen array of claim 1, wherein the allergen or set of of different allergens is coupled covalently or non-covalently, preferably by passive adsorption.

7. The antigen array of claim 1, wherein the solid carrier is a sheet or plate of a porous or non-porous material, preferably a nitrocellulose sheet, more preferably a laminated nitrocellulose sheet.

8. The antigen array of claim 1, wherein the array comprises at least 25 different groups, wherein each group is fixed as an addressable element in a rectangular array, optionally at densities of 1 addressable element per $mm^2$.

9. The antigen array of claim 8, wherein each group of allergen-coated beads comprises:
   (i) beads coated with one allergen, or
   (ii) beads coated with a set of different allergens, preferably an allergen extract.

10. The antigen array of claim 1, wherein the antigen array is contained in a cartridge comprising a test chamber for the antigen array, a reservoir for liquid waste, and optionally a barcode.

11. The antigen array of claim 10, wherein the cartridge is contained in an apparatus comprising a chamber for one or more cartridges, a pipettor and a device for signal detection.

12. A kit comprising an antigen array according to claim 1, a detection reagent, one or more buffers, one or more control samples, and instructions for using the kit, and optionally a signal generation reagent.

13. A method of detecting an immunoglobulin specific for a allergen or for a set of different allergens comprising:
   (i) providing an antigen array according to claim 1,
   (ii) incubating the array with a sample,
   (iii) incubating the array with a detection reagent,
   (iv) optionally incubating the array with a signal generation reagent, and
   (v) measuring a detectable signal.

14. The method of claim 13, wherein the immunoglobulin is an IgE antibody associated with allergy or an IgG antibody associated with an infection or an autoimmune disease.

15. The method of claim 13, wherein the sample is a biological fluid, preferably serum, whole or processed blood, nasal fluid or urine, a cell lysate or a tissue homogenate from a subject or a pool of subjects.

16. The method of claim 13, wherein the detection reagent is an affinity binder specific for the immunoglobulin, preferably an antibody, an aptamer or an affibody, optionally wherein the detection reagent is:
   (i) directly labeled, preferably with a colored or fluorescent compound or with gold nanoparticles or colored latex nanoparticles; or
   (ii) conjugated to an enzyme.

17. The method of claim 13, further comprising incubating the antigen array with a signal generation reagent according to step (iv) of claim 13, wherein the detection reagent is conjugated to an enzyme and the signal generation reagent comprises a substrate for said enzyme.

18. The method of claim 13, further comprising incubating the antigen array with a stop solution following step (iv) of claim 13.

19. The method of claim 13, wherein the immunoglobulin is an IgE antibody associated with allergy and the detection reagent is an IgE-specific antibody or IgE-specific aptamer.

* * * * *